Figure 1:
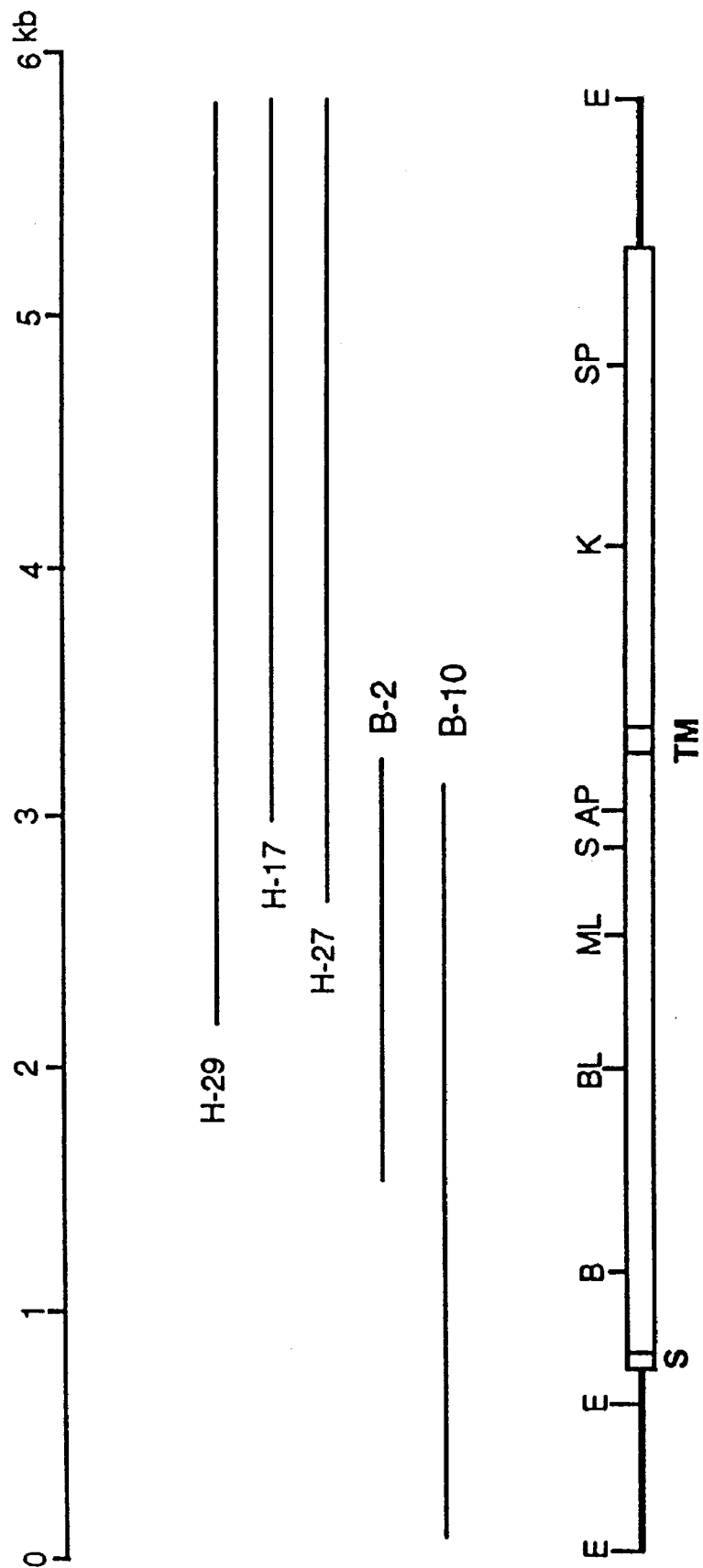

US005840842A

United States Patent [19]
Schlessinger et al.

[11] Patent Number: 5,840,842
[45] Date of Patent: Nov. 24, 1998

[54] RECEPTOR-TYPE PHOSPHOTYROSINE PHOSPHATASE-SIGMA

[75] Inventors: Joseph Schlessinger; Hai Yan, both of New York, N.Y.

[73] Assignee: New York University, New York, N.Y.

[21] Appl. No.: 447,464

[22] Filed: May 24, 1995

Related U.S. Application Data

[62] Division of Ser. No. 130,570, Oct. 1, 1993, abandoned.

[51] Int. Cl.$^6$ .................................................. C07K 14/705
[52] U.S. Cl. ......................... 530/350; 530/300; 536/23.1; 536/23.5; 435/7.1; 435/69.1; 435/252.3; 435/196; 435/325; 435/320.1; 435/194
[58] Field of Search ..................................... 530/300, 350; 536/23.1, 23.5, 196; 435/7.1, 69.1, 252.3, 370.1, 194

[56] References Cited

U.S. PATENT DOCUMENTS 4,710,469  12/1987  Liang et al. ............................. 435/194

FOREIGN PATENT DOCUMENTS

WO92/01050  1/1992  WIPO .

OTHER PUBLICATIONS

Mizuno et al, (1993) 13:5513–5573.
Yan et al., A Novel Receptor Tyrosine Phosphatase–σ that is Highly Expressed in the Nervous System. J. Biol. Chem. 268:24880–24886 (1993).
Pan et al., Cloning and expression of two structurally distinct receptor–linked protein–tyrosine phosphatases generated by RNA processing from a single gene. J. Biol. Chem. 268:19284–19291 (1993).
Walton et al., A novel receptor type protein tyrosine phosphatase is expressed during neurogenesis in the olfactory neuroepithelium. Neuron 11:387–400 (1993).
Jiang et al., Cloning and characterization of R–PTP–k, a new member of the receptor protein tyrosine phosphatase family with a proteolytically cleaved cellular adhesion molecule–like extracellular region. Mol. Cell Biol. 13:2942–2951 (1993).
Yu et al., The N–terminal and C–terminal domains of a receptor tyrosine phosphatase are associated by non–covalent linkage. Oncogene 7:1051–1057 (1992).
LaForgia et al., Receptor protein–tyrosine phosphatase gamma is a candidate tumor suppressor gene at human chromosome region 3p21. Proc. Natl. Acad. Sci. USA 88:5036–5040 (1991).
Daum et al., Characterization of a human recombinant receptor–linked protein tyrosine phosphatase, J. Biol. Chem., 266:12211–12215 (1991).
Gebbink et al., Cloning, expression and chromosomal localization of a new putative receptor–like protein tyrosine phosphatase, FEBS Lett. 290:123–130 (1991).

Kaplan et al., Cloning of three human tyrosine phosphatases reveals a multigene family of receptor–linked protein–tyrosine–phosphatases expressed in brain, Proc. Natl. Acad. Sci. USA 87:7000–7004 (1990).
Sap et al., Cloning and expression of a widely expressed receptor tyrosine phosphatase, Proc. Natl. Acad. Sci. USA 87:6112–6116 (1990).
George and Parker, Preliminary characterization of phosphotyrosine phosphatase activities in human peripheral blood lymphocytes: Identification of CD45 as a phosphotyrosine phosphatase, J. Cell Biochem. 42:71–81 (1990).
Nishi et al., Novel putative protein tyrosine phosphatases identified by the polymerase chain reaction. FEBS Lett. 271:178–180. (1990).
Jirik et al., Cloning of a novel receptor–linked protein tyrosine phosphatase from a human hepatoblastoma cell line, FASEB J. 4A:2082 (Abst. 2253) (1990).
Jirik et al., Cloning and chromosomal assignment of a widely expressed human receptor–like protein–tyrosine phosphatase, FEBS Lett. 273:239–242 (1990).
Krueger et al., Structural diversity and evolution of human receptor–like protein tyrosine phosphatases, EMBO J. 9:3241–3252 (1990).
Matthews et al., Identification of an additional member of the protein–tyrosine phosphatase family:Evidence for alternative splicing in the tryosine phosphatase domain, Proc. Natl. Acad. Sci. USA 87:4444–4448 (1990).
Ohagi et al., Sequence of a cDNA encoding human LRP (leukocyte common antigen–related peptide), Nucl. Acids Res. 18:7159 (1990).
Streuli et al., Distinct functional roles of the two intracellular phosphatase like domains of the receptor–linked protein tyrosine phosphatases LCA and LAR, EMBO J. 9:2399–2407 (1990).
Streuli et al., A new member of the immunoglobulin superfamily that has a cytoplasmic region homologous to the leukocyte common antigen, J. Exp. Med. 168:1523–1530 (1988).
Tonks et al., Demonstration that the leukocyte common antigen CD45 is a protein tyrosine phosphatase, Biochemistry 27:8695–8701 (1988).
Charbonneau et al., The leukocyte common antigen (CD45): A putative receptor–linked protein tyrosine phosphatase, Proc. Natl. Acad. Sci. USA 85:7182–7186 (1988).

(List continued on next page.)

*Primary Examiner*—Stephen Walsh
*Assistant Examiner*—Kenneth A. Sorensen

[57] ABSTRACT

The present invention relates to a novel receptor-type protein tyrosine phosphatase protein or glycoprotein, termed RPTPσ (also known as RPTPase-σ), DNA coding therefor, antibodies specific for the protein or glycoprotein, methods for production and identification of the protein, methods for detection of nucleic acid encoding the protein, and methods for screening compounds capable of binding to and either inhibiting or stimulating RPTPσ phosphatase activity.

3 Claims, 21 Drawing Sheets

OTHER PUBLICATIONS

Ralph et al., Structural variants of human T200 glycoprotein (leukocyte–common antigen), EMBO J. 6:1251–1257 (1987).

Tian et al., Three receptor–linked protein–tyrosine phosphates are selectively expressed on central nervous systems axons in the Drosophila embryo. Cell 67:675–685 (1991).

Yang et al., Two Drosophila receptor–like tyrosine phosphatase genes are expressed in a subset of developing axons and pioneer neurons in the embryonic CNS. Cell 67:661–673 (1991).

Hariharan et al., Cloning and characterization of a receptor–class phosphotyrosine phosphatase gene expressed on central nervous system axons in *Drosophila melanogaster*, Proc. Natl. Acad. Sci. USA 88:11266–11270 (1991).

Streuli et al., A family of receptor–linked protein tyrosine phosphatases in humans and Drosophila, Proc. Natl. Acad. Sci. USA 86:8698–8702 (1989).

Zheng et al., Cell transformation and activation of $pp60^{c-src}$ by overexpression of a protein tyrosine phosphatase. Nature 359:336–339 (1992).

Haughn et al., Association of tyrosine kinase $p56^{lck}$ with CD4 inhibits the induction of growth through the $\alpha\beta$ T–cell receptor. Nature 358:328–331 (1992).

Mustelin et al., Rapid activation of the T–cell tyrosine protein kinase pp56lck by the CD45 phosphotyrosine phosphatase, Proc. Natl. Acad. Sci. USA 86:6302–6306 (1989).

O'Dell et al., Long–term potentiation in the hippocampus is blocked by tyrosine kinase inhibitors. Nature 353:558–560 (1991).

Ostergaard et al., Expression of CD45 alters phosphorylation of the lck–encoded tyrosine protein kinase in murine lymphoma T–cell lines, Proc. Natl. Acad. Sci. USA 86:8959–8963 (1989).

Klarlund, Transformation of cells by an inhibitor of phosphatases acting on phosphotyrosine in proteins, Cell 41:707–717 (1985).

Mauro et al., Homophilic and heterophilic binding activities of Nr–CAM, a nervous system cell adhesion molecule. J. Cell Biol. 119:191–202 (1992).

O'Bryan et al., axl, a transforming gene isolated from primary human myeloid leukemia cells, encodes a novel receptor tyrosine kinase. Mol. Cell. Biol. 11:5016–5031 (1991).

Rescigno et al., A putative receptor tyrosine kinase with unique structural topology. Oncogene 6:1909–1913 (1991).

Bieber et al., Drosophila neuroglian: a member of the immunoglobulin superfamily with extensive homology to the vertebrate neural adhesion molecule L1. Cell 59:447–460 (1989).

Edelman et al., Cellular expression of liver and neural cell adhesion molecules after transfection with their cDNAs results in specific cell–cell binding. Proc. Natl. Acad. Sci. 84:8502–8505 (1987).

Moos et al., Neural adhesion molecule L1 as a member of the immunoglobin superfamily with binding domains similar to fibronectin. Nature 334:701–703 (1988).

Barthels et al., Isolation and nucleotide sequence of mouse NCAM cDNA that codes for a $M_r$ 79 000 polypeptide without a membrane spanning–region. EMBO J. 6:907–914 (1987).

Kornblihtt et al., Primary structure of human fibronectin: differential splicing may generate at least 10 polypeptides from a single gene. EMBO J. 4:1755–1759 (1985).

Nakagawara et al., Association between high levels of expression of the TRK gene and favorable outcome in human neuroblastoma. N. Eng. J. Med. 328:847–854 (1993).

Schlessinger and Ullrich, Growth factor signaling by receptor tyrosine kinases. Neuron 9:383–391 (1992).

Charbonneau and Tonks, 1002 protein phosphatases. Ann Rev. Cell Biol. 8:463–493 (1992).

Chao, Growth factor signaling: where is the specificity? Cell 68:995–997 (1992).

Chao, Neurotrophin receptors: a window into neuronal differentiation. Neuron 9:583–593 (1992).

Pot and Dixon, A thousand and two protein tyrosine phosphatases, Biochem. Biophys. Acta. 1136:35–43 (1992).

Grumet, Cell adhesion molecules and their subgroups in the nervous system. Curr. Opin. Neurol. 1:370–376 (1991).

Fischer et al., Protein tyrosine phosphatases: A diverse family of intracellular and transmembrane enzymes, Science 253:401–406 (1991).

Saito et al., Molecular characterization of protein tyrosine phosphatase, Cell Growth Differ. 2:59–65 (1991).

Klausner and Samelson, T cell antigen receptor activation pathways: The tyrosine kinase connection. Cell 64:875–878 (1991).

Ullrich and Schlessinger, Signal transduction by receptors with tyrosine kinase activity. Cell. 61:203–212 (1990).

Yarden and Ullrich, Growth factor receptor tyrosine kinases. Ann. Rev. Biochem. 57:443–478 (1988).

Williams, A year in the life of the immunoglobin superfamily. Immunol. Today 8:298–303 (1987).

Hunter et al., Protein–tyrosine kinases. Ann. Rev. Biochem. 54:897–930 (1985).

Pot et al., Cloning, Bacterial Expression, Purification and Characterization of the Cytoplasmic Domain of Rat LAR a Receptor–like Protein Tyrosine Phosphatase. J. Biol. Chem. 266(29):19688–19696 (Oct. 1991).

Sambrook et al., Section 16.3 in "Molecular Cloning a Laboratory Manual" 2nd. ed. Cold Spring Harbor Laboratory Press (1989).

Sakimura et al., Molecular cloning and the nucleotide sequence of cDNA to mRNA for non–neuronal enolase ($\alpha\alpha$) enolase of rat brain and liver. Nuc. Acids Res. 13(12):4365–4378 (1985).

```
  1  GGCACGAGCC AGACACTAGC TGAAAAGTCA GGTGACAGAA ACAATGATTC
 51  AGACTGATCA CATGATTACA AAGCTGGGGG CTCCAGCAGG GCTCCAGGTG
101  GTCGGGGTGG ACATCTAAGG AAGCAGTGAC ATGGGAGGGG CAAGCACTGG
151  GCCAGCCTTG AGCCGCCTGG ATGACAGAGA CAGAGGATCT GGTAGCTCCA
201  GGGATCTCCG GTCCATGCCT TACTTGGCCA GGGGTTCCT GAAGGACCTG
251  CCGGCAAACT TGGCTTTGCT GCCCAGCTCC TCCTCGATTC TAAGGATCTG
301  ATTGTACTTG GCCAGGCGCT CAGATCGGCA GGGGCACCA GTCTTGATCT
351  GCCCAGTGCA GAGCCCCACC ACCAGGTCGG CAATGAAAGT GTCCTCAGTC
401  TCCCCAGATC GATGGGACAC CATGACACCC CAGCCATTGG ACTGGGCCAG
451  CTTACACGCC TGCAGAGACT CGGTCACAGA GCCAATCTGG TTCACTTTGA
501  GCAGGAGGCA GTTGCAGGAC TTTTGCCCTG CAGCCTTGGC GATCCGCTTA
551  GGGTTGGTCA CTGTGAGGTC ATCCCCCACC ACCTGGATGC CTGCAGTAGC
601  TGTGAACTTC TGCCAAGCAT CCCAGTCGTC CTGGTCAAAG GGATCTTCAA
651  TGGACACCAC TGGGTAGTCC TTGATGAAGG ACTTGTACAG GTCGGCCAGC
```

FIG.2a

```
701   TGGTCGGGTG TGATGTACCG GCTGGCATCA TCTGGAGACT TGAAGTCCAG

751   GTCATACTTG CCAGCCCTGT AGAATTCGGA GGCAGCCACA TCCATCCCCC

801   ACCAGGGCGG AGGCTGGAGG CCACTGCCAA GC ATG GCG CCC ACC TGG
                                          Met Ala Pro Thr Trp>
                                            *

848   AGA CCC AGC GTG TCT GTG GTG GGT CCT GTG GGG CTC TTC
 6    Arg Pro Ser Val Ser Val Val Gly Pro Val Gly Leu Phe>

890   CTT GTA CTG CTG GCC AGA GGG TGC TTG GCT GAA GAG CCA CCC
 20   Leu Val Leu Leu Ala Arg Gly Cys Leu Ala Glu Glu Pro Pro>

932   AGA TTT ATC AGA GAG CCC AAG GAT CAG ATT GGT GTG TCA GGA
 34   Arg Phe Ile Arg Glu Pro Lys Asp Gln Ile Gly Val Ser Gly>

974   GGC GTG GCC TCC TTC GTG TGC CAG GCC ACA GGT GAC CCT AAG
 48   Gly Val Ala Ser Phe Val Cys Gln Ala Thr Gly Asp Pro Lys>

1016  CCA CGG GTG ACC TGG AAC AAG AAG GGC AAA AAG GTG AAC TCA
 62   Pro Arg Val Thr Trp Asn Lys Lys Gly Lys Lys Val Asn Ser>

1058  CAG CGC TTT GAG ACC ATT GAC TTT GAC GAG AGC TCG GGG GCC
 76   Gln Arg Phe Glu Thr Ile Asp Phe Asp Glu Ser Ser Gly Ala>

1100  GTG CTG AGG ATC CAG CCA CTT CGG ACA CCC CGG GAT GAG AAC
 90   Val Leu Arg Ile Gln Pro Leu Arg Thr Pro Arg Asp Glu Asn>
```

FIG.2b

| | | | | | | | | | | | | | |
|---|---|---|---|---|---|---|---|---|---|---|---|---|---|
| 1142<br>104 | GTG<br>Val | TAC<br>Tyr | GAG<br>Glu | TGT<br>Cys | GTG<br>Val | GCC<br>Ala | CAG<br>Gln | AAC<br>Asn | TCG<br>Ser | GTG<br>Val | GGG<br>Gly | GAG<br>Glu | ATC<br>Ile | ACA<br>Thr⟩ |
| 1184<br>118 | GTT<br>Val | CAT<br>His | GCG<br>Ala | AAG<br>Lys | CTC<br>Leu | ACC<br>Thr | GTC<br>Val | CTG<br>Leu | CGA<br>Arg | GAG<br>Glu | GAC<br>Asp | CAG<br>Gln | CTG<br>Leu | CCT<br>Pro⟩ |
| 1226<br>132 | CCT<br>Pro | GGC<br>Gly | TTC<br>Phe | CCC<br>Pro | AAC<br>Asn | ATT<br>Ile | GAC<br>Asp | ATG<br>Met | GGC<br>Gly | CCC<br>Pro | CAG<br>Gln | TTG<br>Leu | AAG<br>Lys | GTT<br>Val⟩ |
| 1268<br>146 | GTA<br>Val | GAG<br>Glu | CGC<br>Arg | ACA<br>Thr | CGC<br>Arg | ACA<br>Thr | GCC<br>Ala | ATG<br>Met | CTC<br>Leu | TGT<br>Cys | GCT<br>Ala | GCC<br>Ala | AGC<br>Ser⟩ | |
| 1310<br>160 | GGA<br>Gly | AAC<br>Asn | CCT<br>Pro | GAC<br>Asp | CCT<br>Pro | GAG<br>Glu | ATC<br>Ile | ACC<br>Thr | TGG<br>Trp | TTC<br>Phe | AAG<br>Lys | GAC<br>Asp | TTC<br>Phe | CTG<br>Leu⟩ |
| 1352<br>174 | CCT<br>Pro | GTG<br>Val | GAC<br>Asp | CCC<br>Pro | AGT<br>Ser | GCC<br>Ala | AAT<br>Asn | GGG<br>Gly | CGG<br>Arg | ATC<br>Ile | AAG<br>Lys | CAG<br>Gln | CTT<br>Leu⟩ | |
| 1394<br>188 | CGG<br>Arg | TCA<br>Ser | GGT<br>Gly | GCC<br>Ala | CCC<br>Pro | CTG<br>Leu | CAG<br>Gln | ATT<br>Ile | GAG<br>Glu | AGC<br>Ser | AGC<br>Ser | GAG<br>Glu | ACA<br>Thr | GAC<br>Asp⟩ |
| 1436<br>202 | CAG<br>Gln | GGC<br>Gly | AAG<br>Lys | TAC<br>Tyr | GAG<br>Glu | TGT<br>Cys | GTG<br>Val | GCC<br>Ala | AAC<br>Asn | AGC<br>Ser | ACC<br>Thr | AGC<br>Ser | GCT<br>Ala | GGG<br>Gly | GTG<br>Val⟩ |
| 1478<br>216 | CGC<br>Arg | TAC<br>Tyr | TCA<br>Ser | CCT<br>Pro | GCC<br>Ala | AAC<br>Asn | CTC<br>Leu | TAC<br>Tyr | GTG<br>Val | CGA<br>Arg | GTC<br>Val | AGC<br>Arg | CGT<br>Arg⟩ | |
| 1520<br>230 | GTG<br>Val | GCC<br>Ala | CCC<br>Pro | CGC<br>Arg | TTC<br>Phe | TCC<br>Ser | ATC<br>Ile | CTG<br>Leu | CCC<br>Pro | ATG<br>Met | AGC<br>Ser | CAC<br>His | GAG<br>Glu | ATC<br>Ile⟩ |

FIG.2c

```
1562  ATG CCC GGT GGG AAT GTG AAT ATC ACT TGT GTG GCT GTG GGC
 244  Met Pro Gly Gly Asn Val Asn Ile Thr Cys Val Ala Val Gly>

1604  TCA CCC ATG CCC TAC GTG AAG TGG ATG CAG GGG GCA GAG GAC
 258  Ser Pro Met Pro Tyr Val Lys Trp Met Gln Gly Ala Glu Asp>

1646  CTG ACG CCT GAG GAT GAC ATG CCC GTG GGT CGG AAT GTC CTC
 272  Leu Thr Pro Glu Asp Asp Met Pro Val Gly Arg Asn Val Leu>

1688  GAA CTC ACG GAT GTC AAA GAC TCA GCC AAC TAT ACT TGT GTG
 286  Glu Leu Thr Asp Val Lys Asp Ser Ala Asn Tyr Thr Cys Val>

1730  GCC ATG TCC AGC CTG GGA CTC CTC GAG ATC GTT GCT CAG ATC
 300  Ala Met Ser Ser Leu Gly Val Leu Glu Ile Val Ala Gln Ile>

1772  ACT GTA AAA TCT CTC CCC AAA GCC CCT GGG ACT CCC GTG GTG
 314  Thr Val Lys Ser Leu Pro Lys Ala Pro Gly Thr Pro Val Val>

1814  ACG GAG AAC ACT GCT ACC AGT ATC ATC GTC ACA TGG GAC TCA
 328  Thr Glu Asn Thr Ala Thr Ser Ile Ile Val Thr Trp Asp Ser>

1856  GGC AAT CCT GAC CCT GTG TCC TAC TAC GTA ATT GAG TAT AAA
 342  Gly Asn Pro Asp Pro Val Ser Tyr Tyr Val Ile Glu Tyr Lys>

1898  TCC AAA AGC CAG GAT GGG CCG TAT CAG ATC AAA GAA GAC ATC
 356  Ser Lys Ser Gln Asp Gly Pro Tyr Gln Ile Lys Glu Asp Ile>
```

FIG.2d

| 1940 | ACC | ACC | ACG | CGC | TAC | AGC | ATC | GGC | GGC | CTG | AGC | CCC | AAC | TCT |
| --- | --- | --- | --- | --- | --- | --- | --- | --- | --- | --- | --- | --- | --- | --- |
| 370 | Thr | Thr | Thr | Arg | Tyr | Ser | Ile | Gly | Gly | Leu | Ser | Pro | Asn | Ser> |
| 1982 | GAG | TAT | GAG | ATC | TGG | GTG | TCA | GCT | GTC | AAC | TCC | ATC | GGC | CAG |
| 384 | Glu | Tyr | Glu | Ile | Trp | Val | Ser | Ala | Val | Asn | Ser | Ile | Gly | Gln> |
| 2024 | GGC | CCC | CCC | AGT | GAG | TCG | GTG | GTG | ACC | CGC | ACA | GGC | GAG | CAG |
| 398 | Gly | Pro | Pro | Ser | Glu | Ser | Val | Val | Thr | Arg | Thr | Gly | Glu | Gln> |
| 2066 | GCA | CCA | GCC | AGT | GCT | CCC | AGG | AAT | GTT | CAG | GCG | CGC | ATG | CTC |
| 412 | Ala | Pro | Ala | Ser | Ala | Pro | Arg | Asn | Val | Gln | Ala | Arg | Met | Leu> |
| 2108 | AGT | GCC | ACC | ATG | ATT | GTG | CAG | TGG | CAG | GAG | CCC | GTG | GAG |
| 426 | Ser | Ala | Thr | Met | Ile | Val | Gln | Trp | Gln | Glu | Pro | Val | Glu> |
| 2150 | CCC | AAT | GGC | CTG | ATC | CGT | GGC | TAC | GTC | TAC | TAC | ACC | ATG |
| 440 | Pro | Asn | Gly | Leu | Ile | Arg | Gly | Tyr | Val | Tyr | Tyr | Thr | Met> |
| 2192 | GAG | CCC | GAG | CAT | CCG | GTG | GGC | AAC | TGG | CAG | AAG | CAC | AAT | GTG |
| 454 | Glu | Pro | Glu | His | Pro | Val | Gly | Asn | Trp | Gln | Lys | His | Asn | Val> |
| 2234 | GAC | GAC | AGT | CTT | CTG | ACC | GTG | GGC | AGC | CTG | CTA | GAG | GAT |
| 468 | Asp | Asp | Ser | Leu | Leu | Thr | Val | Gly | Ser | Leu | Leu | Glu | Asp> |
| 2276 | GAG | ACC | TAC | ACT | GTG | AGA | GTG | CTC | GCC | TTC | ACA | TCG | GTG | GGC |
| 482 | Glu | Thr | Tyr | Thr | Val | Arg | Val | Leu | Ala | Phe | Thr | Ser | Val | Gly> |
| 2318 | GAT | GGG | CCA | CTG | TCA | GAC | CCC | ATC | CAG | GTC | AAG | ACC | CAG | CAG |
| 496 | Asp | Gly | Pro | Leu | Ser | Asp | Pro | Ile | Gln | Val | Lys | Thr | Gln | Gln> |

FIG.2e

| | | | | | | | | | | |
|---|---|---|---|---|---|---|---|---|---|---|
| 2360 | GGA | GTG | CCC | GGC | CAG | CCC | ATG | AAC | TTG | CGG | GCT | GAG | GCC | AAG |
| 510 | Gly | Val | Pro | Gly | Gln | Pro | Met | Asn | Leu | Arg | Ala | Glu | Ala | Lys> |
| 2402 | TCA | GAG | ACC | AGC | ATT | GGG | CTC | TCG | TGG | AGT | GCA | CCA | CGG | CAG |
| 524 | Ser | Glu | Thr | Ser | Ile | Gly | Leu | Ser | Trp | Ser | Ala | Pro | Arg | Gln> |
| 2444 | GAG | AGT | GTC | ATT | AAG | TAT | GAA | CTG | CTC | TTC | CGG | GAG | GGC | GAC |
| 538 | Glu | Ser | Val | Ile | Lys | Tyr | Glu | Leu | Leu | Phe | Arg | Glu | Gly | Asp> |
| 2486 | CGA | GGC | CGA | GAG | GTG | GAC | CTC | AAG | CCC | CGA | ACC | TTC | GAC | CCA | ACC | ACA | GCC |
| 552 | Arg | Gly | Arg | Glu | Val | Asp | Leu | Lys | Pro | Arg | Thr | Phe | Asp | Pro | Thr | Thr | Ala> |
| 2528 | TTT | GTG | GTG | GAG | GAC | CTC | AAG | CCC | AAT | ACG | GAG | TAC | GCG | TTC |
| 566 | Phe | Val | Val | Glu | Asp | Leu | Lys | Pro | Asn | Thr | Glu | Tyr | Ala | Phe> |
| 2570 | CGG | CTG | GCG | GCT | CGC | TCG | CCG | CAG | GGC | CTG | GGC | GCC | TTC | ACC |
| 580 | Arg | Leu | Ala | Ala | Arg | Ser | Pro | Gln | Gly | Leu | Gly | Ala | Phe | Thr> |
| 2612 | GCG | GTT | GTG | CGC | CAG | CGC | ACA | CTG | CAG | GCC | ATC | TCC | CCC | AAG |
| 594 | Ala | Val | Val | Arg | Gln | Arg | Thr | Leu | Gln | Ala | Ile | Ser | Pro | Lys> |
| 2654 | AAC | TTC | AAG | GTG | AAG | ATG | ATC | ATG | AAA | ACT | TCA | GTG | CTG | CTA |
| 608 | Asn | Phe | Lys | Val | Lys | Met | Ile | Met | Lys | Thr | Ser | Val | Leu | Leu> |
| 2696 | AGC | TGG | GAG | TTC | CCT | GAC | AAC | TAT | AAC | TCA | CCC | ACG | CCC | TAC |
| 622 | Ser | Trp | Glu | Phe | Pro | Asp | Asn | Tyr | Asn | Ser | Pro | Thr | Pro | Tyr> |

FIG.2f

```
2738  AAG ATC CAG TAC AAT GGA CTC ACA CTG GAC GTG GAT GGC CGC
 636  Lys Ile Gln Tyr Asn Gly Leu Thr Leu Asp Val Asp Gly Arg>

2780  ACT ACC AAG AAG CTG ATC ACG CAC CTC AAG CCA CAC ACC TTC
 650  Thr Thr Lys Lys Leu Ile Thr His Leu Lys Pro His Thr Phe>

2822  TAT AAC TTC GTG CTC ACC AAC CGT GGC AGC AGC CTG GGA GGC
 664  Tyr Asn Phe Val Leu Thr Asn Arg Gly Ser Ser Leu Gly Gly>

2864  CTG CAG CAG ACG GTC ACC GCC AGG ACC GCC TTC AAC ATG CTC
 678  Leu Gln Gln Thr Val Thr Ala Arg Thr Ala Phe Asn Met Leu>

2906  AGT GGC AAG CCT AGT GTC GCC CCA AAG CCT GAC AAC GAT GGT
 692  Ser Gly Lys Pro Ser Val Ala Pro Lys Pro Asp Asn Asp Gly>

2948  TCC ATT GTG GTC TAC CTG CCT GAT GGC CAG AGT CCC GTG ACA
 706  Ser Ile Val Val Tyr Leu Pro Asp Gly Gln Ser Pro Val Thr>

2990  GTG CAG AAC TAC TTC ATT GTG ATG GTC CCA CTT CGG AAG TCT
 720  Val Gln Asn Tyr Phe Ile Val Met Val Pro Leu Arg Lys Ser>

3032  CGT GGT GGC CAG TTC CCT ATC CTA GGT AGT CCA GAG GAC
 734  Arg Gly Gly Gln Phe Pro Ile Leu Gly Ser Pro Glu Asp>

3074  ATG GAT CTG GAG GAG CTC ATC CAG GAC CTC TCC CGG CTG CAG
 748  Met Asp Leu Glu Glu Leu Ile Gln Asp Leu Ser Arg Leu Gln>
```

FIG.2g

FIG.2h

```
3116  AGG CGC AGC CTG CGC CAC TCA AGA CAG CTG GAG GTG CCT CGG
 762  Arg Arg Ser Leu Arg His Ser Arg Gln Leu Glu Val Pro Arg>

3158  CCT TAC ATC GCC GCT CGG TTC TCC ATC CTG CCA GCT GTC TTC
 776  Pro Tyr Ile Ala Ala Arg Phe Ser Ile Leu Pro Ala Val Phe>

3200  CAT CCT GGG AAC CAG AAG CAA TAT GGT GGC TTT GAC AAC AGG
 790  His Pro Gly Asn Gln Lys Gln Tyr Gly Gly Phe Asp Asn Arg>

3242  GGC TTG GAG CCA GGC CAC CGT TAT GTC CTC TTT GTA CTT GCT
 804  Gly Leu Glu Pro Gly His Arg Tyr Val Leu Phe Val Leu Ala>

3284  GTG CTG CAG AAG AAT GAG CAG CCT ACA TTT GCA GCC AGT CCC TTC
 818  Val Leu Gln Lys Asn Glu Gln Pro Thr Phe Ala Ala Ser Pro Phe>

3326  TCA GAC CCC TTC CAA CTG GAC AAC CCA GAC CCG CAG CCC ATT
 832  Ser Asp Pro Phe Gln Leu Asp Asn Pro Asp Pro Gln Pro Ile>

3368  GTG GAT GGC GAG GAG CTC ATC TGG GTG ATC GGG CCC GTG
 846  Val Asp Gly Glu Glu Leu Ile Trp Val Ile Gly Pro Val>

3410  CTG GCC GTG GTC TTC ATC ATC TGC ATC GTA ATT GCC ATC CTG
 860  Leu Ala Val Val Phe Ile Ile Cys Ile Val Ile Ala Ile Leu>

3452  CTG TAC AAG AAC CCT GAC AGC AAA CGC AAG GAC TCA GAG
 874  Leu Tyr Lys Asn Lys Pro Asp Ser Lys Arg Lys Asp Ser Glu>

3494  CCC CGC ACC AAA TGC TTA TTG AAC GCA GAC CTC GCC CCC
 888  Pro Arg Thr Lys Cys Leu Leu Asn Ala Asp Leu Ala Pro>
```

```
3536  CAT CAC CCC AAG GAC CCT GTG GAA ATG CGA CGT ATC AAC TTC
902   His His Pro Lys Asp Pro Val Glu Met Arg Arg Ile Asn Phe>

3578  CAG ACG CCA GGT ATG CTC AGC CAC CCG ATT CCC ATC ACA
916   Gln Thr Pro Gly Met Leu Ser His Pro Pro Ile Pro Ile Thr>

3620  GAC ATG GCT GAA CAC ATG GAG AGA CTC AAA GCC AAC GAC AGC
930   Asp Met Ala Glu His Met Glu Arg Leu Lys Ala Asn Asp Ser>

3662  CTC AAG CTC TCC CAG GAG TAT GAG TCC ATC GAC CCT GGC CAG
944   Leu Lys Leu Ser Gln Glu Tyr Glu Ser Ile Asp Pro Gly Gln>

3704  CAG TTC ACT TGG GAA CAT TCG AAC CTG GAG GCC AAC AAG CCA
958   Gln Phe Thr Trp Glu His Ser Asn Leu Glu Ala Asn Lys Pro>

3746  AAG AAC CGA TAC GCC AAT GTC ATC GCC TAT GAC CAT TCA CGA
972   Lys Asn Arg Tyr Ala Asn Val Ile Ala Tyr Asp His Ser Arg>

3788  GTC ATC CTG CAG CCT TTA GAA GGC ATC GGT ATG AGT GAT TAC
986   Val Ile Leu Gln Pro Leu Glu Gly Ile Met Gly Ser Asp Tyr>

3830  ATC AAT GCC AAC TAT GTG GAC GGC TAT CGG CGG CAG AAC GCA
1000  Ile Asn Ala Asn Tyr Val Asp Gly Tyr Arg Arg Gln Asn Ala>

3872  TAC ATC GCC ACG CAG GGG CCC CTC CCT GAA ACC TTT GGG GAC
1014  Tyr Ile Ala Thr Gln Gly Pro Leu Pro Glu Thr Phe Gly Asp>
```

FIG.2i

```
3914  TTC TGG CGG ATG GTG TGG GAG CAG CGG TCA GCC ACT GTG GTC
1028  Phe Trp Arg Met Val Trp Glu Gln Arg Ser Ala Thr Val Val>

3956  ATG ACA CGG CTG GAG GAG AAA CGG GTC AAA TGT GAC
1042  Met Met Thr Arg Leu Glu Glu Lys Arg Val Lys Cys Asp>

3998  CAG TAC TGG CCT AAC CGA GGC ACA GAG TAC GGC TTC ATC
1056  Gln Tyr Trp Pro Asn Arg Gly Thr Glu Tyr Gly Phe Ile>

4040  CAG GTC ACC CTA CTA GAT ACT ATG GAG CTG GCC ACC TTC TGT
1070  Gln Val Thr Leu Leu Asp Thr Met Glu Leu Ala Thr Phe Cys>

4082  GTC AGG ACC TTT TCT CTA CAC AAG AAT GGC TCT AGT GAG AAG
1084  Val Arg Thr Phe Ser Leu His Lys Asn Gly Ser Ser Glu Lys>

4124  CGT GAG GTA CGA CAT TTT CAG TTC ACA GCA TGG CCT GAC CAC
1098  Arg Glu Val Arg His Phe Gln Phe Thr Ala Trp Pro Asp His>

4166  GGG GTA CCC GAG TAC CCC ACA CCC CTG GCG TTT CTG CGC
1112  Gly Val Pro Glu Tyr Pro Thr Pro Leu Ala Phe Leu Arg>

4208  AGA GTC AAG ACC TGC AAC CCG CCT GAC GCT GGC CCA GTT GTG
1126  Arg Val Lys Thr Cys Asn Pro Pro Asp Ala Gly Pro Val Val>

4250  GTC CAC TGC AGC GCG GGT GTG GGG CGT ACT GGC TGC TTC ATT
1140  Val His Cys Ser Ala Gly Val Gly Arg Thr Gly Cys Phe Ile>

4292  GTA ATT GAT GCC ATG ATG TTG GAG CGC ATC AGA ACA GAG AAG ACC
1154  Val Ile Asp Ala Met Met Leu Glu Arg Ile Arg Thr Glu Lys Thr>
```

FIG.2j

```
4334  GTG GAT GTG TAC GGA CAC GTG ACA CTC ATG CGG TCA CAG CGC
1168  Val Asp Val Tyr Gly His Val Thr Leu Met Arg Ser Gln Arg>

4376  AAC TAC ATG GTG CAG ACA GAG GAT CAG TAT AGC TTC ATC CAC
1182  Asn Tyr Met Val Gln Thr Glu Asp Gln Tyr Ser Phe Ile His>

4418  GAG GCA CTG CTG GAG GCT GTG GGC TGT GTG AAT ACC GAG GTC
1196  Glu Ala Leu Leu Glu Ala Val Gly Cys Val Gly Asn Thr Glu Val>

4460  CCC GCG CGC AGC CTC TAC ACC TAT TAT ATC CAG AAG CTG GCC CAG
1210  Pro Ala Arg Ser Leu Tyr Thr Tyr Tyr Ile Gln Lys Leu Ala Gln>

4502  GTG GAG CCT GGC GAG GTC CAT GTC ACA GGA ATG GAG CTT GAG TTC
1224  Val Glu Pro Gly Glu Val His Val Thr Gly Met Glu Leu Glu Phe>

4544  AAG AGG CTT GCC AGC TCC AAG GCA CAC ACT TCG AGA TTC ATC
1238  Lys Arg Leu Ala Ser Ser Lys Ala His Thr Ser Arg Phe Ile>

4586  ACT GCC AGC CTG CCT TGC AAC AAG TTT AAC CGC CTG GTG
1252  Thr Ala Ser Leu Pro Cys Asn Lys Phe Asn Arg Leu Val>

4628  AAC ATC CTG CCG TAC GAG AGC TCG CGT GTC TGC CTG CAG CCC
1266  Asn Ile Leu Pro Tyr Glu Ser Arg Val Cys Leu Gln Pro>

4670  ATT CGT GGT GTC GAG GGC TCT GAC TAC ATC AAT GCC AGC TTC
1280  Ile Arg Gly Val Glu Gly Ser Asp Tyr Ile Asn Ala Ser Phe>

4712  ATC GAC GGC TAC AGA CAG CAG AAA GCC TAC ATT GCA ACG CAG
1294  Ile Asp Gly Tyr Arg Gln Gln Lys Ala Tyr Ile Ala Thr Gln>
```

FIG.2k

| | | | | | | | | | | | | | |
|---|---|---|---|---|---|---|---|---|---|---|---|---|---|
| 4754 1308 | GGT Gly | CCA Pro | CTG Leu | GCA Ala | GAG Glu | ACC Thr | ACA Thr | GAG Glu | GAC Asp | TTC Phe | TGG Trp | CGT Arg | GCC Ala | CTG Leu |
| 4796 1322 | TGG Trp | GAG Glu | AAC Asn | AAC Asn | TCC Ser | ACT Thr | ATT Ile | GTG Val | GTA Val | ATG Met | CTC Leu | ACC Thr | AAG Lys | CTC Leu |
| 4838 1336 | CGC Arg | GAG Glu | ATG Met | GGC Gly | CGG Arg | GAG Glu | AAG Lys | TGC Cys | CAC His | CAG Gln | TAC Tyr | TGG Trp | CCA Pro | GCT Ala |
| 4880 1350 | GAG Glu | CGC Arg | TCT Ser | GCC Ala | CGC Arg | TAC Tyr | CAG Gln | TAC Tyr | TTT Phe | GTG Val | GTT Val | GAC Asp | CCG Pro | ATG Met |
| 4922 1364 | GCA Ala | GAG Glu | TAT Tyr | AAC Asn | ATG Met | CCA Pro | CAG Gln | TAC Tyr | ATT Ile | CTG Leu | CGT Arg | GAG Glu | TTT Phe | AAG Lys |
| 4964 1378 | GTC Val | ACA Thr | GAT Asp | GCC Ala | CGG Arg | GAT Asp | GGC Gly | CAG Gln | TCC Ser | CGG Arg | ACC Thr | GTC Val | CGA Arg | CAG Gln |
| 5006 1392 | TTC Phe | CAG Gln | TTC Phe | ACG Thr | GAC Asp | TGG Trp | CCA Pro | GAG Glu | CAG Gln | CAG Gln | GGT Gly | GCA Ala | CCC Pro | AAG Lys | TCA Ser |
| 5048 1406 | GGG Gly | GAA Glu | GGC Gly | TTC Phe | ATT Ile | GAC Asp | TTC Phe | ATC Ile | GGC Gly | CAA Gln | GTG Val | CAT His | AAG Lys | ACC Thr |
| 5090 1420 | AAG Lys | GAG Glu | CAG Gln | TTT Phe | GGC Gly | CAG Gln | GAT Asp | GGC Gly | CCC Pro | ATC Ile | TCG Ser | GTG Val | CAC His | TGT Cys |

FIG. 21

```
5132  AGT GCT GGA GTG GGC AGG ACC GGA GTA TTC ATC ACT CTG AGC
1434  Ser Ala Gly Val Gly Arg Thr Gly Val Phe Ile Thr Leu Ser>

5174  ATC GTG CTG GAG CGA ATG CGC TAC GAG GGG GTG GTG GAC ATT
1448  Ile Val Leu Glu Arg Met Arg Tyr Glu Gly Val Val Asp Ile>

5216  TTC CAG ACA GTG AAG GTG CTT CGG ACC CAG CGG CCT GCC ATG
1462  Phe Gln Thr Val Lys Val Leu Arg Thr Gln Arg Pro Ala Met>

5258  GTG CAG ACA GAG TAC CAG TTC TGC TTC CAG GCG GCG
1476  Val Gln Thr Glu Tyr Gln Phe Cys Phe Gln Ala Ala>

5300  TTG GAA TAC CTG GGC AGC TTT GAT CAT TAT GCA ACA TAA GC
1490  Leu Glu Tyr Leu Gly Ser Phe Asp His Tyr Ala Thr

5341  CATGGGCCCC GCCCAACACC TCGACCCAGC TCCAAGTGCC CTGAATGTGA
5391  GCCCAGCCCT CGGTGCTGGG TGGGAGGCGG CCCAGGGAGG AAACCTCCTC
5441  TCCCTGGAGA CAGGCACTGC CTTCGGAAGG GCACATTCCT CATTCCCTCC
5491  TGACTCCAAA ACGAGGTTCC AGGGTGGGGG GTAGGGTGGA GAGTAGAGGA
5541  GGCACTGCTC CCCATAGCTG GGGTCACAAG GGACAGAACT CTGCTCCCAC
5591  ACTTCCCTGC CTGCCTGTCA GCAACATTCT TTTTTTCCAT TTTTTAATA
5641  GTGTATTTTT TTTCTTCATC TTTCTTTTT TTTTTAAAA AAAAAAAAA
```

FIG.2m

```
Sigma  (1)  33   PRFIREPKDQIGVSGGVASFVCQATGDPKPR VTWNKK GKKVNS  QRFETIDFDE        SSGAVLRIQPLRTPRDENVYECVAQNSVGEIT VHAKLTV    124
Sigma  (2) 135   PNIDMGPQLKYVERTRTATMLCAASGNPDPE ITWFKD FLPVDP  SASNGRIKQL        RSGA LQIESSEET DQGKYECVATNSAGVRYSSPANLYV    225
Sigma  (3) 232   PRFSILPWSHE IMPGGNVNITCVAVGSPMPY VKWMCG AEDLTP                   EDDMPVGRNVLELTDVK   DSANYTCVAMSSLGVIE AVAQITV  315
rLAR   (1)  23   PVFVKVPEDQTGLSGGVASFVCQATGEPKPR ITWMKK GKKVSS  QRFEVIEFDD        GAGSVLRIQPLRVQRDEAIYECTATNSLGEIN TSAKLSV    114
mNCAM  (1)  20   LQVDIVPSQGEISVGESKFFLCQVAGDAKDKDISWFSPNGEKLSPNQQRISVWNDDD         SSTLTIYNANI DDAGIYKCVVTAEDGT Q SEATVNV     92
```

FIG. 3

```
Sigma (1) 320  KAPGTPVVTENTATSITVT WDSG..NPDPVSYYVIEYKSKSQD..GPYQIKEDITTTRYSIGGLSPNSEYEIWSAVNSIGQGPPS ESVVTRTGEQ   (411)
      (2) 415  SAPRN VQARMLSATTMIVQMEEPVEPNGLIRGYRVYYTMEPEHPVGNMQKHNVDDSLLTTVGSLLEDETYTVRVLAFTSVGDGPLS DPIQVKTQQG   (510)
      (3) 513  GQPMNLRAEAKSETSIGLS WSAP..RQESVIKYELLFR.EGDR..GREVGRTFDPTTAFVVEDLKPNTEYAFR LAARSPQGLGAFTAVVRQRTLQA  (603)
      (4) 604  ISPKNFKVKMIMKTSVLLS WEFPDNYNSPTP YKIQYNGLTLDVDGR........TTKKLITHLKPHTFYNFV LTNRGSSLGGLQ QTVTARTAFN   (689)
      (5) 693  GKPSVAPKPDNDGSIVVYLPDGQSPVTVQN    YFIVMVPLRKSRGGQFPILLGSPEDMDL EELIQDLSRLQRRSLRHSRQLEVPRPYIAARFSILP   (786)
rLAR  (1) 310  KPPIDLVVTETTATSVTLT WDSG..NTEPVSFYGIQYRAAGTD..GPFQEVDGVASTRYSIGGLSPFSEYAFRVLAVNSIGRGPPS EAVRARTGEQ   (401)
hFnIII-7       SPPTNLHLEANPDTGVLTVSMERSITPD...ITGYRITTTPTNGQQGNSLEEVVHADQSSCTFDNLSPGLEYNVSVYTVKDDKESVPIS       DTIIP
```

FIG.4

RECEPTOR-TYPE PHOSPHOTYROSINE PHOSPHATASE-SIGMA

This is a divisional of application Ser. No. 08/130,570 filed Oct. 1, 1993, now abandoned.

TABLE OF CONTENTS
1. INTRODUCTION
2. BACKGROUND OF THE INVENTION
    2.1. Phosphototyrosine Kinases (PTKs)
    2.2. Protein Tyrosine Phosphates (PTPs)
3. SUMMARY OF THE INVENTION
4. DESCRIPTION OF THE FIGURES
5. DETAILED DESCRIPTION OF THE INVENTION
    5.1. RPTPσ
    5.2. THE RPTPσ CODING SEQUENCE
    5.3. EXPRESSION OF RPTPσ AND GENERATION
        5.3.1. EXPRESSION SYSTEMS
        5.3.2. IDENTIFICATION OF TRANSFECTANTS OR TRANSFORMATS THAT EXPRESS THE RPTPσ
        5.3.3. RPTPσ ANALOGS
    5.4. RPTPσ ANTIBODY PRODUCTION AND SCREENING
    5.5. USES OF RPTPσ CODING SEQUENCE
    5.6. USES OF RPTPσ CODING SEQUENCE IN DIGNOSTICS AND THERAPEUTICS
    5.7. USE OF RPTPσ OR LINGANDS
6. EXAMPLE: ISOLATION AND ANALYSIS OF RAT RPTPσ cDNA CLONES
    6.1. Isolation Of Novel PTPase Domains From Total RNA Of PC12 Cells By PCR
    6.2. Library Screening And Isolation Of cDNA Clones
    6.3. Sequence Alignments
    6.4. Results and Discussion
        6.4.1. Molecular Cloning of the full-length cDNA for RPTPσ
        6.4.2. Characterization of RPTPσ
7. EXAMPLE: EXPRESSION AND TISSUE DISTRIBUTION OF RPTPσ
    7.1. Methods
        7.1.1. RNA Isolation And Northern Blot Analysis
        7.1.2. IN SITU Hybridization
        7.1.3. Generation Of Antibodies Against RPTPσ-GST Fusion Proteins And Peptide Derived From RPTPσ
    7.2. Results And Discussion
        7.2.1. Distribution Of RPTPσ mRNA
        7.2.2. IN SITU Hybridization
        7.2.3. Transient Expression Of RPTPσ
8. EXAMPLE: CHROMOSOMAL LOCALIZATION OFTHE MURINE RPTPσGENE

1. INTRODUCTION

The present invention, in the field of biochemistry and cell and molecular biology, relates to a novel receptor-type protein tyrosine phosphatase protein or glycoprotein, termed RPTPσ (also known as RPTPase-σ),DNA coding therefor, antibodies specific for the protein or glycoprotein, methods for production and identification of the protein, methods for detection of nucleic acid encoding the protein, and methods for screening compounds capable of binding to and either inhibiting or stimulating RPTPσ phosphatase activity.

2. BACKGROUND OF THE INVENTION

Tyrosine phosphorylation of proteins is involved in an increasing number of cellular signalling events and is critical for regulation of normal cell growth, proliferation and differentiation. It was originally implicated in signalling by paracrine- or autocrine- acting growth factors, and endocrine hormones such as insulin (see Yarden, Y. et al., *Annu. Rev. Biochem.* 57:443–478 (1988) for review). It is now clear that this posttranslational modification is also involved in diverse processes such as the activation of cells of the immune system by antigens (Klausner, R. D. et al., *Cell* 64:875–878), signalling by lymphokines (Hatakeyama, M. et al., 1991 *Science* 252:1523–1528 (1991); Mills, G. B. et al., *J. Biol. Chem.* 265:3561–3567 (1990)), and cellular differentiation and survival (Fu, X. Y. 1992 *Cell* 70:323–335; Schlessinger, J. et al. 1992 *Neuron* 9:1–20; Velazquez, L. et al., 1992 *Cell* 70:313–322). Links are also emerging between tyrosine phosphorylation and the processes of cell adhesion and cell-cell contact.

The identification of several growth factor receptors and retroviral oncogenes as tyrosine-specific protein kinases indicated that protein phosphorylation on tyrosine residues plays a key role in cellular growth control. This notion is bolstered by the observation that the level of tyrosine phosphorylation of enzymes important in signal transduction (such as phospholipase C) correlates with their increased activity upon growth factor stimulation, thus establishing a functional role for tyrosine phosphorylation (Ullrich, A., et al., *Cell* 15 61:203–212 (1990)).

Most of the processes in which tyrosine phosphorylation is implicated involve the transduction of a signal through the cell membrane. This can occur through dimerization-mediated activation of members of the receptor tyrosine kinase family by soluble ligands (reviewed in Ullrich, A. et al., supra). However, receptor tyrosine kinase activity is also modulated by membrane-bound ligands on neighboring cells, as in the case of the interaction between the sevenless kinase and the bride of sevenless protein (Rubin, G. M. 1991, *Trends in Genet.* 7:372–376).

The degree and pattern of phosphorylation of tyrosine residues on cellular proteins are regulated by the opposing activities of protein-tyrosine kinases (PTKases; ATP:protein-tyrosine O-phosphotransferase, EC 2.7.1.112) and protein-tyrosine-phosphatases (PTPases; protein-tyrosine-phosphate phosphohydrolase, EC 3.1.3.48). The structural characteristics and evolution of PTKases as well as their role in the regulation of cell growth have been reviewed (Hunter, T., et al., *Annu. Rev. Biochem.* 54:897–930 (1985); Ullrich, A., et al., supra).

2.1. Phosphotyrosine Kinases (PTKs)

Tyrosine kinases comprise a discrete family of enzymes having common ancestry with, but major differences from, serine/threonine-specific protein kinases (Hanks, S. K. et al., (1988) *Science* 241:42–52). The mechanisms leading to changes in activity of tyrosine kinases are best understood for receptor-type tyrosine kinases which have a transmembrane topology (Ullrich, A. et al., supra). With such kinases, the binding of specific ligands to the extracellular domain of these enzymes is thought to induce their oligomerization leading to an increase in tyrosine kinase activity and activation of the signal transduction pathways (Ullrich, A. et al., supra). The importance of this activity is supported by the knowledge that dysregulation of kinase activity through mutation or over-expression is a mechanism for oncogenic transformation (Hunter, T. et al., supra; Ullrich, A. et al., 1990, supra).

Tyrosine phosphorylation initiated by several receptor tyrosine kinases has been implicated, for example, in neuronal cell proliferation and differentiation (Chao, M. V.

(1992) Cell 68:995–997). These include the receptors for neurotrophic factors belonging to the trk family of receptor tyrosine kinases, as well as PDGF and FGF receptor tyrosine kinases (Chao, M. V. (1992) Neuron 9:583–593). It has been demonstrated that there is an association between favorable outcome in human neuroblastoma and high level expression of the tyrosine kinases, (Nakagawara, A. et al. (1993) N England J Med 328:847–854. Virtually nothing is known about the control of tyrosine phosphorylation by protein tyrosine phosphatases in the mammalian nervous system.

The existence of receptor-like tyrosine kinases with an extracellular domain similar to cell adhesion molecules of the CAM-family (e.g., Axl and Ark (O'Bryan, J. P. et al., 1991 Mol. Cell. Biol. 11:5016–5031; Rescigno, J. et al., 1991 Oncogene 6:1909–1913)) implicates tyrosine phosphorylation as a broadly employed direct, downstream effector mechanism for precise cell-cell recognition and signalling events. Non-receptor type tyrosine kinases are in some cases associated with other proteins having a transmembrane topology, e.g., Lck kinase and the CD4 protein or Fyn kinase and T-cell receptor complex components (Haughn, L. et al., 1992 Nature 358:328–331; Samelson, L. E. et al., 1992 Proc. Natl. Acad. Sci. USA 87:4358–4362; Veillette, A. et al., 1988 Cell 55:301–308). However, the mechanism by which kinase activity is modulated in these instances is not understood.

2.2. Protein Tyrosine Phosphatases (PTPs)

The PTPs are composed of at least two very distinct broad categories: the protein serine/threonine phosphatases and the protein tyrosine phosphatases (Hunter, T. Cell, 58:1013–1016 (1989)). In contrast to phosphatases, protein kinases have greater sequence similarity between serine/threonine-specific and tyrosine-specific enzymes. To date, more than 26 PTPs have been identified (Saito, H. et al. (1991) Cell Growth & Differentiat. 2:59–65; Charbonneau, H. et al. (1992) Annu. Rev. Cell Biol. 8:463–493). The known enzymes can be divided into two groups; a cytosolic form and a receptor-type form with a single transmembrane domain (receptor-type PTP or RPTP).

Most RPTPs contain two conserved catalytic tyrosine phosphatase (PTPase) domains each of which encompasses a segment of 240 amino acid residues (Saito et al., supra; Charbonneau et al., supra). The catalytic domain contains a highly conserved motif of 11 amino acid residues, (I/V) HCXAGXXR(S/T)G (SEQ. ID NO:1), in which the cysteine residue is essential for protein tyrosine phosphatase activity (Streuli, M. et al., (1990) EMBO J. 9:2399–2407; Pot, D. A. et al. (1992) J. Biol. Chem. 267:140–143; Wang, Y. et al. (1991) EMBO J. 10:3231–3237).

The RPTPs can be subclassified into five types based upon the amino acid sequence diversity of their extracellular domains (Fisher et al., supra; Saito et al., supra; Charbonneau et al., supra; Krueger, N. K. et al. (1992) Proc. Natl. Acad. Sci. USA 89:7417–7421; Barnea, G. et al., (1993) Mol. Cell. Biol. 13:1497- 1506). Type II RPTPs are characterized by the presence of both immunoglobulin (Ig)-like and fibronectin type III (FNIII)-like repeats in the extracellular domain. Thus, they resemble the N-CAM family of cell adhesion molecules (Cunningham, B. A. et al., (1987) Science 236:799–806; Barthers, D. et al., (1987) EMBO J. 6:907–914; Edelman, G. M. et al. (1991) Annu. Rev. Biochem. 60:155–190; Grumet, M. (1991) Curr. Opin. Neurobiol. 1:370–376) and may therefore function as cell adhesion molecules. Examples of such RPTPs include LAR (Streuli, M. et al., (1988)J. Exp. Med.168:1523–1530; Yu, Q. et al., (1992) Oncogene 7:1051–1057; Streuli, M. et al., (1989) Proc. Natl. Acad. Sci. USA 86:8698–8702), PTPμ (Gebbink, M. F. B. G. et al., (1991) FEBS Lett. 290:123–130) and PTPκ (Jiang, Y. P. et al., (1993) Mol. Cell. Biol. 13:2942–2951 and DPTP (Streuli, M. et al., (1989), supra).

An analysis of the expression pattern of several RPTPs in the developing Drosophila CNS suggests some function of these molecules in aspects of axon guidance and outgrowth (Tian, S. S. et al., 1991 Cell 67:675–685; Yang, X. et al., 1991, Cell 67:661–673), an observation which might be related to the ability of RPTPs to control the activity of src-family tyrosine kinases (Mustelin, T. et al., 1989, Proc. Natl. Acad. Sci. USA 86:6302–6306; Ostergaard, H. L. et al., 1989, Proc. Natl. Acad. Sci. USA 86:8959–8963; Zheng, X. M. et al., 1992, Nature 359:336–339).

Certain RPTPs may function as tumor suppressor genes, for example, by controlling contact inhibition (LaForgia, S. et al., 1991 Proc. Natl. Acad. Sci. USA 88:5036–5040). Elevation of cellular phosphotyrosine may occur through mechanisms other than the activation of a tyrosine kinase itself. For instance, expression of the v-crk oncogene, though not a tyrosine kinase, induces the phosphorylation of tyrosine residues through a poorly understood mechanism (Mayer, B. J. et al. (1988) Nature 332:272–275). Potentially, such an outcome could result from either mutation of the substrate or through a general decrease in cellular phosphatase activity, especially in view of the normally high turnover rate of cellular tyrosine-phosphate (Sefton, B. M. et al. (1980) Cell 20:807–816). The latter possibility is suggested by the demonstration that tyrosine phosphatase inhibitors can "reversibly transform" cells (Klarlund, J. K. Cell 41: 707–717 (1985)). PTPases could therefor act as recessive oncogenes. While we are beginning to understand more about the structure and diversity of the PTPases, much remains to be learned about their cellular functions. Thus, a better understanding of, and an ability to control, phosphotyrosine metabolism requires knowledge not only the role of tyrosine kinase activity, but also of the action of PTP family enzymes as well. It is clear in the art that further delineation of structure-function relationships among cytoplasmic and receptor type PTPasses are needed to gain important understanding of the mechanisms of cell growth, differentiation, and oncogenesis.

3. SUMMARY OF THE INVENTION

The present invention relates to a novel mammalian receptor-type protein tyrosine phosphatase-σ (RPTPσ) protein or glycoprotein molecule, functionally equivalent derivatives of RPTPσ, and analogs of the RPTPσ. Further, the present invention relates to DNA encoding such RPTPσ proteins and their derivatives and antibodies directed to RPTPσ proteins, and/or RPTPσ functionally equivalent derivatives and RPTPσ analogs. Still further, the present invention relates to methods for the production and identification of RPTPσ proteins, functionally equivalent derivatives, and analogs, methods for detection of nucleic acid encoding the RPTPσ proteins and derivatives, and methods for screening compounds capable of binding to and either inhibiting or stimulating RPTPσ biological activity, e.g., its enzymatic phosphatase activity. Preferably, the nucleic acid molecule encodes human RPTPσ or encodes a functional derivative thereof. The DNA molecule is preferably cDNA or genomic DNA. The invention is further directed to the DNA molecule in the form of an expression vehicle, as well as prokaryotic and eukaryotic host cells having the DNA molecule.

4. DESCRIPTION OF THE FIGURES

FIG. 1 shows a restriction map of rat cDNA clone encoding RPTPσ. The thin lines indicate several overlapping cDNA clones; both strands of each were sequenced. Unfilled area represents the open reading frame for RPTPσ containing the putative signal peptide (S) and transmembrane domain (TM). The thick lines indicate the 5' and 3' untranslated sequences. Restriction sites are: E (EcoRI), B (BamHI), BL (BglII), ML(MluI), S (StuI), AP (Asp700), K (Kpn I), SP (Spl I). A scale bar in kilobase (kb) is at the top.

FIG. 2(A)–2(M) shows the nucleotide sequence (SEQ ID NO:2) and deduced amino acid sequence (SEQ ID NO:3) of rat RPTPσ. The predicted translation initiation site is indicated by an asterisk. The translation stop site is double-underlined. The predicted signal peptide and transmembrane regions are underlined and two tandem tyrosine phosphatase domains are boxed. Three-letter amino acid code is used.

FIG. 3 shows a proposed alignment of three Iglike domains of RPTPσ (SEQ ID NO:3) to the first Ig-like domain of rat LAR (SEQ ID NO:4) (Yu, Q. et al., (1992) Oncogene 7:1051–1057) and mouse N-CAM (SEQ ID NO:5) (Barthers, D. et al., (1987) EMBO J. 6:907–914). The residue numbers of the initial and end amino acids of each repeat are indicated at left and right. Conserved residues in these repeats are highlighted in bold. The cysteine residues are indicated by asterisks.

FIG. 4 shows a proposed alignment of five fibronectin type III repeats of RPTPσ (SEQ ID NO:3) to the first FN III-like repeat of rat LAR (SEQ ID NO:6) (Yu et al., supra) and to the human fibronectin type III repeat-domain 7 (SEQ ID NO:7) (Kornblihtt, A. R. et al., (1985) EMBO J. 4:1755–1759). The residue numbers of the initial and end amino acids of each repeat are indicated at the left and right (except for human FNIII-7). Conserved residues in these repeats are highlighted in bold.

Figure 5:
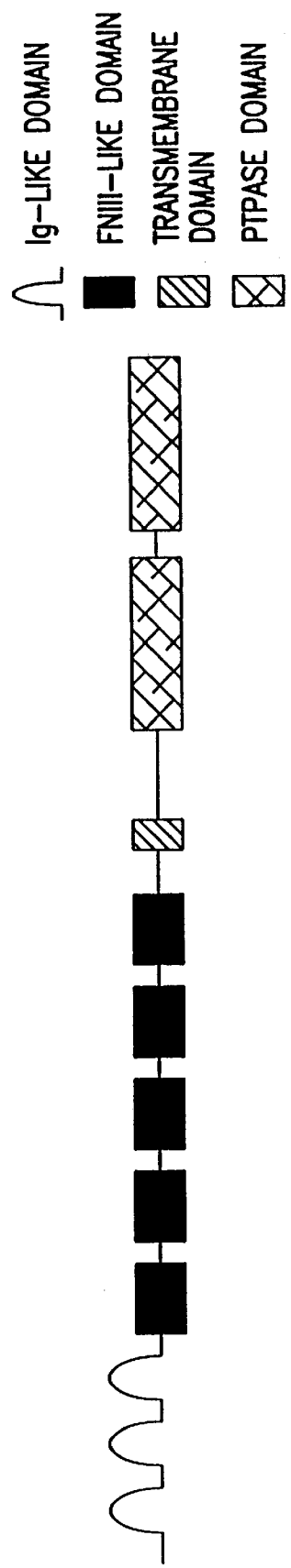

FIG. 5 shows a schematic representation of RPTPσ indicating the possible different functional domains.

Figure 6:
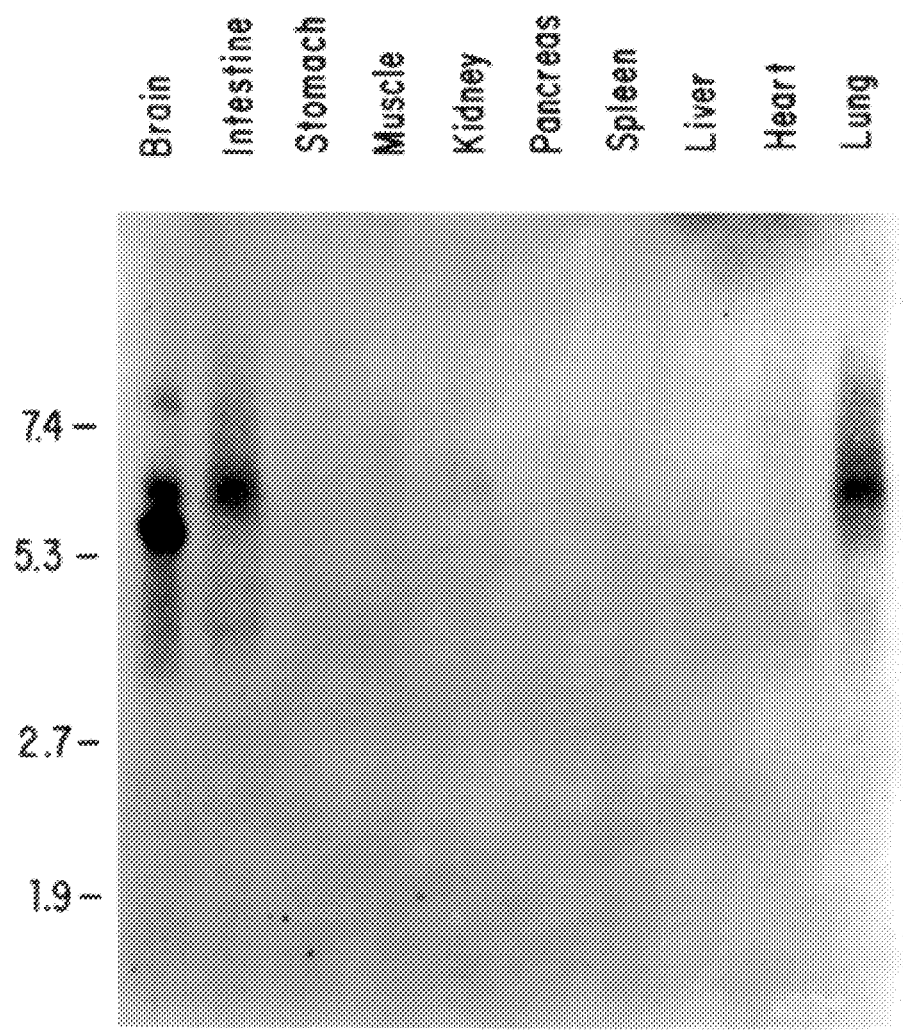

FIG. 6 shows the results of Northern blot analysis of RPTPσ expression in postnatal rat tissues. The blot was hybridized with a cDNA probe encoding amino acid residue 408 to 521 of the extracellular domain of RPTPσ. The RNA size in kilobase (kb) is shown on the left.

Figure 7A:
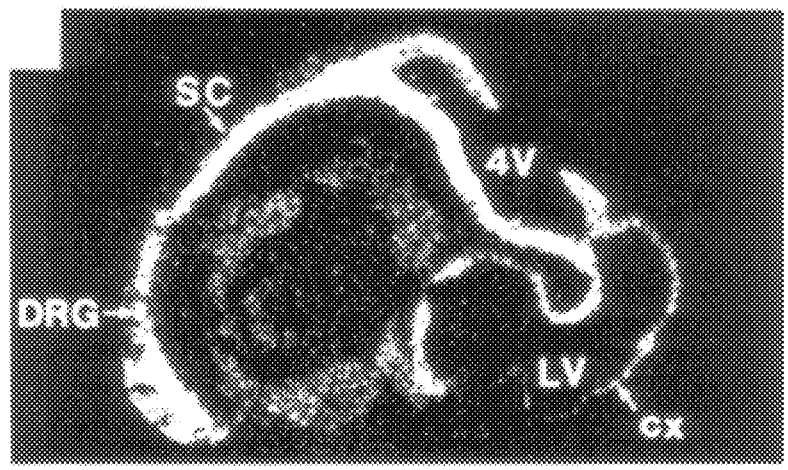
Figure 7B:
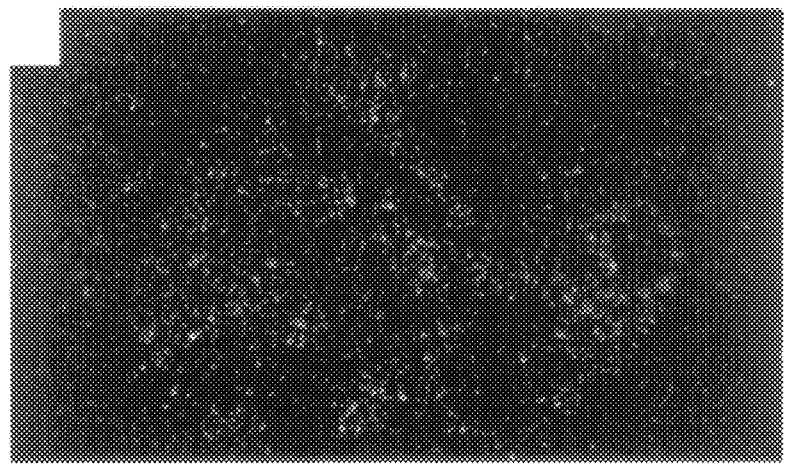
Figure 7C:
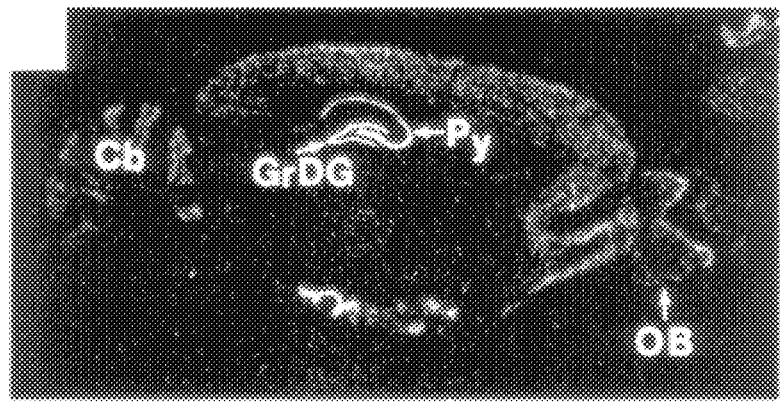
Figure 7D:
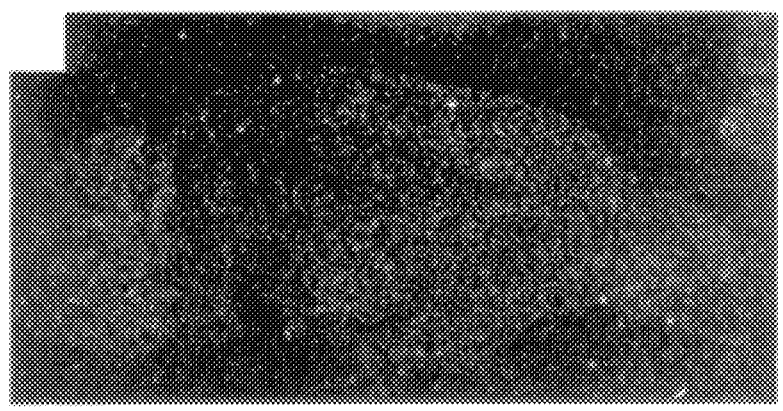

FIG. 7(A)–7(D) are a series of micrographs showing results of in situ hybridization analysis of RPTPσ expression in rat. FIG. 7(A) is a sagittal section of whole rat at embryonic day 12 (E 12) was hybridized with labelled "probe-1". cx, cortical neuroepithelium; 4 V, 4th ventricle; LV, lateral ventricle; SC, spinal cord; DRG, dorsal root ganglia. FIG. 7(C) is a sagittal section of adult rat brain to which was hybridized labelled probe-1. Cb, cerebellum; Py, pyramidal cell layer; GrDG, granular layer of dentate gyrus; OB, olfactory bulb. FIG. 7(B) and 7(D) show tissue sections adjacent to the sections depicted in FIG. 7(A) and FIG. 7(C), respectively, which were hybridized with labelled probe-1 in the presence of a 70-fold excess of unlabelled oligomer to demonstrate the specificity of in situ hybridization.

Figure 8A:
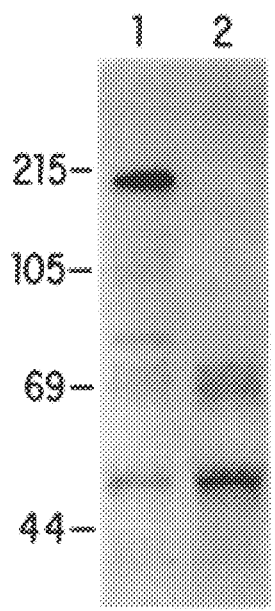
Figure 8B:
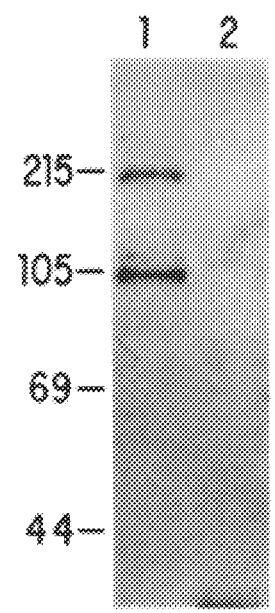

FIG. 8 shows transient expression of RPTPσ in human embryonic kidney 293 cells. Panel A shows results of immunoprecipitation and immunoblot of RPTPσ. Cells were transiently transfected with RKsigma or RKSigmaR. Supernatants of lysates were immunoprecipitated with polyclonal FNIII Ab and then immunoblotted with same antibodies. Lane 1, lysate from cells transfected with RKSigma; lane 2, lysate from cells transfected with RKSigmaR. Panel B shows an immunoblot analysis of RPTPσ with polyclonal FNIII Ab. Lane 1 and lane 2 are same as in Panel A. Molecular mass markers are shown in kDa.

5. DETAILED DESCRIPTION OF THE INVENTION

5.1. RPTPσ

Through the use of recombinant DNA methods, a novel mammalian receptor-type (transmembrane) protein tyrosine phosphatase (PTPase; EC 3.1.3.48) has been identified and cloned from a rat brain stem cDNA library. In view of its receptor-like structure, and the likelihood that it is part of a family, the protein has been termed, RPTPσ (receptor protein tyrosine phosphatase-σ). The family is designated herein as the "RPTPσs." The amino acid sequence of the rat RPTPσ is shown in FIG. 2(A)–2(G) (SEQ ID NO:3). The extracellular segment of rat RPTPσ contains 824 amino acids and is composed of 3 Ig-like and 5 fibronectin type III (FNIII)-like repeats. The 627 amino acid cytoplasmic region of rat RPTPσ consists of two catalytic domains oriented in tandem. In addition to being composed of intracellular domains having enzymatic activity, the receptor family to which RPTPs belong includes transmembrane proteins having and N-terminal extracellular domains, analogous to the tyrosine kinase enzyme family (Tonks, N. K. et al. (1988) Biochemistry 27:8695–8701; Charbonneau, H. et al. (1988) Proc. Natl. Acad. Sci. USA 85:7182–7186; Streuli, M. et al. (1988) J. Exp. Med. 168:1523–2530; Streuli, M. et al. (1989) Proc. Natl. Acad. Sci. USA 86:8698–8702). It is concluded, therefore, that ligands in the extracellular environment can control the activity of this membrane-associated subclass of PTPases.

The cDNA cloning of rat RPTPσ and the complete DNA and amino acid sequences of rat RPTPσ are described herein in the Working Example presented in Section 6, below. Further, Northern analysis, as demonstrated in the Working Example presented in Section 7, below, has been used to identify the natural expression of RPTPσ in various rat tissues.

Briefly, rat RPTPσ is highly expressed in the brain as a 5.7 kb transcript. Rat RPTPσ is also expressed in the lung and intestine as a 6.9 kb transcript but at significantly lower level. Further, RPTPσ is expressed in anatomically distinct regions of rat brain and its expression is developmentally regulated. In situ hybridization studies confirm that RPTPσ is localized predominantly in the nervous system and can be detected in the rat as early as embryonic day 12 (E12). During embryonic development, RPTPσ is expressed extensively in the central and peripheral nervous systems, including the trigeminal and dorsal root ganglia as well as retina. In adult rat brain, expression is restricted primarily to the olfactory tubercle, cerebellum, and hippocampus. Within the latter structure, RPTPσ is present in the pyramidal cell layer and the granular layer of dentate gyrus.

5.2. The RPTPσ Coding Sequence

The nucleotide coding sequence of the rat RPTPσ (SEQ ID NO:2) is depicted in FIG. 2(A)–2(G)). In accordance with the invention, the nucleotide sequence of the RPTPσ protein or its functional equivalent in mammals, including humans, can be used to generate recombinant molecules which direct the expression of RPTPσ; hereinafter, this receptor will be referred to as "RPTPσ", regardless of the species from which it is derived.

The invention also relates to RPTPσ genes isolated from other species, including humans, in which RPTPσ activity exists. Such receptors may demonstrate about 80% overall similarity at the amino acid level, and higher, preferably greater than about 95%, homology within specific highly conserved amino acid sequences.

A bacteriophage cDNA library may be screened, under conditions of reduced stringency, using a radioactively labeled fragment of the mouse RPTPσ clone. Alternatively the mouse RPTPσ sequence can be used to design degenerate or fully degenerate oligonucleotide probes which can be used as PCR (polymerase chain reaction; Mullis, K. et al., *Cold Spring Harbor Symp. Quant. Biol.* 51:263–273 (1986); Erlich, H. et al., EP 50424, EP 84796, EP 258017, EP 237362; Mullis, K., EP 201184; Mullis, K. et al., U.S. Pat. No. 4,683,202; Erlich, H., U.S. Pat. No. 4,582,788; and Saiki, R. et al., U.S. Pat. No. 4,683,194) probes or to screen bacteriophage cDNA libraries. A PCR-based strategy may be used to clone human RPTPσ. Two pools of degenerate oligonucleotides, corresponding to a conserved motifs between the rat RPTPσ and known receptor tyrosine phosphatases, may be designed to serve as primers in a PCR reaction. The template for the reaction is cDNA obtained by reverse transcription of mRNA prepared from cell lines or tissue known to express human RPTPσ. The PCR product may be subcloned and sequenced to insure that the amplified sequences represent the RPTPσ sequences. The PCR fragment may be used to isolate a full length RPTPσ cDNA clone by radioactively labeling the amplified fragment and screening a bacteriophage cDNA library.

Alternatively, the labeled fragment may be used to screen a genomic library. For a review of cloning strategies which may be used, see e.g., Maniatis, 1989, Molecular Cloning, A Laboratory Manual, Cold Springs Harbor Press, New York; and Ausubel et al., 1989, Current Protocols in Molecular Biology, (Green Publishing Associates and Wiley Interscience, New York)

In accordance with the invention, RPTPσ nucleotide sequences which encode RPTPσ, peptide fragments of RPTPσ, RPTPσ fusion proteins or functional equivalents thereof may be used to generate recombinant DNA molecules that direct the expression of RPTPσ protein or a functionally equivalent thereof, in appropriate host cells. Alternatively, nucleotide sequences which hybridize to portions of the RPTPσ sequence may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the RPTPσ protein. Such DNA sequences include those which are capable of hybridizing to the murine RPTPσ sequence under stringent conditions.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the RPTPσ sequence, which result in a silent change thus producing a functionally equivalent RPTPσ. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine; asparagine, glutamine; serine, threonine; phenylalanine, tyrosine.

As used herein, a functionally equivalent RPTPσ may refer to a receptor which exhibits substantially similar biological activity, e.g., is a phosphatase capable of binding to the same or similar ligands as RPTPσ, but not necessarily with the same affinity as native RPTPσ, or, for example, may refer to a structurally similar receptor molecule to which an antibody, preferably a monoclonal antibody, specific to an RPTPσ-family-specific epitope.

The DNA sequences of the invention may be engineered in order to alter the RPTPσ coding sequence for a variety of ends including but not limited to alterations which modify processing and expression of the gene product. For example, mutations may be introduced using techniques which are well known in the art, e.g. site-directed mutagenesis, to insert new restriction sites, to alter glycosylation patterns, phosphorylation, etc. For example, in certain expression systems such as yeast, host cells may over glycosylate the gene product. When using such expression systems it may be preferable to alter the RPTPσ coding sequence to eliminate any N-linked glycosylation site.

In another embodiment of the invention, the RPTPσ or a modified RPTPσ sequence may be ligated to a heterologous sequence to encode a fusion protein. For example, for screening of peptide libraries it may be useful to encode a chimeric RPTPσ protein expressing a heterologous epitope that is recognized by a commercially available antibody. A fusion protein may also be engineered to contain a cleavage site located between the RPTPσ sequence and the heterologous protein sequence, so that the RPTPσ can be cleaved away from the heterologous moiety.

In an alternate embodiment of the invention, the coding sequence of RPTPσ could be synthesized in whole or in part, using chemical methods well known in the art. See, for example, Caruthers, et al., 1980, Nuc. Acids Res. Symp. Ser. 7:215–233; Crea and Horn, 180, Nuc. Acids. Res. 9(10) :2331; Matteucci and Caruthers, 1980, Tetrahedron Letters 21:719; and Chow and Kempe, 1981, Nuc. Acids Res. 9(12):2807–2817. Alternatively, the protein itself could be produced using chemical methods to synthesize the RPTPσ amino acid sequence in whole or in part. For example, peptides can be synthesized by solid phase techniques, cleaved from the resin, and purified by preparative high performance liquid chromatography. (E.g., see Creighton, 1983, Proteins Structures And Molecular Principles, W. H. Freeman and Co., New York. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., New York., pp. 34–49.

5.3. Expression of RPTPσ and Generation of Cell Lines that Express RPTPσ

In order to express a biologically active RPTPσ, the nucleotide sequence coding for RPTPσ, or a functional equivalent as described in Section 5.1 supra, may be inserted into an appropriate expression vector, i.e., a vector which contains the necessary elements for the transcription and translation of the inserted coding sequence. The RPTPσ gene products as well as host cells or cell lines transfected or transformed with recombinant RPTPσ expression vectors can be used for a variety of purposes. These include but are not limited to generating antibodies (i.e., monoclonal or polyclonal) that bind to the receptor, including those that may be capable of competitively inhibiting the binding of RPTPσ ligands to the native RPTPσ, and would thus "neutralize" activity of RPTPσ, and the screening and selection of RPTPσ ligand analogs or drugs that act via the RPTPσ receptor; etc.

5.3.1. Expression Systems

Methods which are well known to those skilled in the art can be used to construct expression vectors containing the RPTPσ coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, New York and Ausubel et al., 1989, Current Protocols in Molecular Biology, Greene Publishing Associates and Wiley Interscience, New York.

A variety of host-expression vector systems may be utilized to express the RPTPσ coding sequence. These include but are not limited to microorganisms such as bacteria transformed with recombinant bacteriophage DNA, plasmid DNA or cosmid DNA expression vectors containing the RPTPσ coding sequence; yeast transformed with recombinant yeast expression vectors containing the RPTPσ coding sequence; insect cell systems infected with recombinant virus expression vectors (e.g., baculovirus) containing the RPTPσ coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the RPTPσ coding sequence; or animal cell systems infected with recombinant virus expression vectors (e.g., adenovirus, vaccinia virus) including cell lines engineered to contain multiple copies of the RPTPσ DNA either stably amplified (CHO/dhfr) or unstably amplified in double-minute chromosomes (e.g., murine cell lines). The expression elements of these systems vary in their strength and specificities. Depending on the host/vector system utilized, any of a number of suitable transcription and translation elements, including constitutive and inducible promoters, may be used in the expression vector. For 25 example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the RPTPσ DNA SV40-, BPV- and EBV-based vectors may be used with an appropriate selectable marker.

In bacterial systems a number of expression 10 vectors may be advantageously selected depending upon the use intended for the RPTPσ expressed. For example, when large quantities of RPTPσ are to be produced for the generation of antibodies or to screen peptide libraries, vectors which direct the expression of high levels of fusion protein products that are readily purified may be desirable. Such vectors include but are not limited to the E. coli expression vector pUR278 (Ruther et al., 1983, EMBO J. 2:1791), in which the RPTPσ coding sequence may be ligated into the vector in frame with the lac Z coding region so that a hybrid AS-lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, New York, Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, New York, Vol. 152, pp. 673–684; and The Molecular Biology of the Yeast Saccharomyces, 1982, Eds, Strathern et al., Cold Spring Harbor Press, Vols. I and II.

In cases where plant expression vectors are used, the expression of the RPTPσ coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be sed to express RPTPσ is an insect system. In one such system, Autoqrapha californica nuclear polyhidrosis virus (ACNPV) is used as a vector to express foreign genes. The virus grows in Spodoptera frugiperda cells. The RPTPσ coding sequence may be cloned into non-essential regions (for example the polyhedrin gene) of the virus and placed under control of an AcNPV promoter (for example the polyhedrin promoter). Successful insertion of the RPTPσ coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the RPTPσ coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing RPTPσ in infected hosts.

(E.g., See Logan & Shenk, 1984, Proc. Natl. Acad. Sci. (USA) 81:3655–3659). Alternatively, the vaccinia 7.5K promoter may be used. (See, e.g., Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931).

Specific initiation signals may also be required for efficient translation of inserted RPTPσ coding sequences. These signals include the ATG initiation codon and adjacent sequences. In cases where the entire RPTPσ gene, including its own initiation codon and adjacent sequences, is inserted into the appropriate expression vector, no additional translational control signals may be needed. However, in cases where only a portion of the RPTPσ coding sequence is inserted, exogenous translational control signals, including the ATG initiation codon, must be provided. Furthermore, the initiation codon must be in phase with the reading frame of the RPTPσ coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the RPTPσ may be engineered. Rather than using expression vectors which contain viral origins of replication, host cells can be transformed with the RPTPσ DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the RPTPσ on the cell surface, and which respond to RPTPσ ligand-mediated signal transduction. Such engineered cell lines are particularly useful in screening RPTPσ ligand analogs.

A number of selection systems may be used, including but not limited to the herpes simplex virus thymidine kinase (Wigler, et al., 1977, Cell 11:223), hypoxanthine-guanine phosphoribosyltransferase (Szybalski & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively.

Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.3.2. Identification of Transfectants or Transformants that Express the RPTPσ

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of RPTPσ MRNA transcripts in the host cell; and (d) detection of the gene product as measured by immunoassay or by its biological activity.

In the first approach, the presence of the RPTPσ coding sequence inserted in the expression vector can be detected by DNA-DNA or DNA-RNA hybridization using probes comprising nucleotide sequences that are homologous to the RPTPσ coding sequence, respectively, or portions or derivatives thereof.

In the second approach, the recombinant expression vector/host system can be identified and selected based upon the presence or absence of certain "marker"gene functions (e.g., thymidine kinase activity, resistance to antibiotics, resistance to methotrexate, transformation phenotype, occlusion body formation in baculovirus, etc.). For example, if the RPTPσ coding sequence is inserted within a marker gene sequence of the vector, recombinants containing the RPTPσ coding sequence can be identified by the absence of the marker gene function. Alternatively, a marker gene can be placed in tandem with the RPTPσ sequence under the control of the same or different promoter used to control the expression of the RPTPσ coding sequence. Expression of the marker in response to induction or selection indicates expression of the RPTPσ coding sequence.

In the third approach, transcriptional activity for the RPTPσ coding region can be assessed by hybridization assays. For example, RNA can be isolated and analyzed by Northern blot using a probe homologous to the RPTPσ coding sequence or particular portions thereof. Alternatively, total nucleic acids of the host cell may be extracted and assayed for hybridization to such probes.

In the fourth approach, the expression of the RPTPσ protein product can be assessed immunologically, for example by Western blots, immunoassays such as radioimmuno-precipitation, enzyme-linked immunoassays and the like. The ultimate test of the success of the expression system, however, involves the detection of the biologically active RPTPσ gene product. A number of assays can be used to detect receptor activity including but not limited to RPTPσ ligand binding assays; and RPTPσ biological assays using engineered cell lines as the test substrate.

5.3.3 RPTPσ Analogs

RPTPσ analogs, i.e., RPTPσ molecules which contain additional chemical moieties not normally a part of the peptide, are also intended to be included within the scope of the present invention. Covalent modifications of the RPTPσ protein or of a peptide derived therefrom, for example, may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate, pH 5.5–7.0, because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine ε-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues may be eamidated to the corresponding glutamyl and aspartyl residues, under mildly acidic conditions. Either form of these residues falls within the scope of this invention.

Derivatization with bifunctional agents is useful for cross-linking the protein or peptide to a water-insoluble support matrix or to other macromolecular carriers. commonly used cross-linking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidyl-propionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the X-amino groups of lysine, arginine, and histidine side chains (T. E. Creighton, *PROTEINS: STRUCTURE AND MOLECULE PROPERTIES*, W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *REMINGTON'S PHARMACEUTICAL SCIENCES*, 18th ed., Mack Publishing Co., Easton, Pa. (1990).

5.4 RPTPσ Antibody Production and Screening

Various procedures known in the art may be used for the production of antibodies to epitopes of the recombinantly produced RPTPσ. Such antibodies include but are not limited to polyclonal, monoclonal, chimeric, single chain, Fab fragments and fragments produced by an Fab expression library. Neutralizing antibodies i.e., those which compete for the RPTPσ ligand binding sites of the RPTPσ molecule are especially preferred for diagnostics and therapeutics. For example, with respect to diagnostics, disorders involving an abnormal level of RPTPσ protein levels may be recognized by the utilization of such antibodies. These disorders may include, but are not limited to, oncogenic disorders associated with an abnormally high net level of kinase activity, such as is seen in human neuroblastomas (Nakagawara, A. et al. (1993) N England J Med 328:847–854.

The antibodies (or fragments thereof) useful in the present invention may be employed histologically, as in immunofluorescence or immunoelectron microscopy, for in situ detection of RPTPσ. In situ detection may be accomplished by removing a histological specimen from a subject, and providing a labeled antibody or antibody fragment of the present invention to such a specimen, preferably by applying or overlaying the antibody over the specimen. Through the use of such a procedure, it is possible to determine not only the presence of RPTPσ but also its distribution in the examined tissue. Using the present invention, those of ordinary skill will readily perceive that any of a wide variety of histological methods (such as staining procedures) can be modified in order to achieve such in situ detection. Such assays for RPTPσ typically comprise incubating a biological sample, such as a biological fluid, a tissue extract, freshly harvested cells, or cells which have been incubated in tissue culture, in the presence of a detectably labeled antibody specific for RPTPσ, and detecting the antibody by any of a number of techniques well-known in the art.

The biological sample may be incubated with a solid phase support or carrier such as nitrocellulose, or other solid support which is capable of immobilizing cells, cell particles or soluble proteins. The support may then be washed with suitable buffers followed by treatment with the detectably labeled RPTPσ-specific antibody. The solid phase support may then be washed with the buffer a second time to remove unbound antibody. The amount of bound label on said solid support may then be detected by conventional means. By "solid phase support" is intended any support capable of binding antigen or antibodies. Well-known supports or carriers include glass, polystyrene, polypropylene, polyethylene, dextran, nylon, amylases, natural and modified celluloses, polyacrylamides, and magnetite. The preferred carrier is totally insoluble in the solution in which the assay of the present invention takes place; partially soluble carriers well-known in the art may also be used. The support material may have virtually any possible structural configuration so long as the support-coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-RPTPσ antibody may be determined according to well-known methods. Those skilled in the art will be able to determine operative and optimal assay conditions for each determination by employing routine experimentation.

One of the ways in which the RPTPσ-specific antibody can be detectably labeled is by linking the antibody, or a second antibody which binds to the anti-RPTPσ antibody, to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, nalate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect RPTPσ through the use of a radioimmunoassay (RIA) (see, for example, Work, T.S. et al., *LABORATORY TECHNIQUES AND BIOCHEMISTRY IN MOLECULAR BIOLOGY*, North Holland Publishing Company, New York, 1978, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing a labeled second antibody (which functions as a "reporter molecule"). After a second incubation period to permit the labeled antibody to complex with the antigen bound to the solid support through the unlabeled antibody, the solid support is washed a second time to remove the unreacted labeled antibody. In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to a fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

Monoclonal antibodies that bind RPTPσ may be radioactively labeled, allowing one to follow their location and distribution in the body after injection. Radioactivity tagged antibodies may be used as a non-invasive diagnostic tool for imaging de novo cells expressing RPTPσ protein, allowing, therefore, for the visualization of the presence of disorders such as neuroblastomas, in which there is an abnormal level of net kinase activity.

Immunotoxins may also be designed which target cytotoxic agents to specific sites in the body. For example, high affinity RPTPσ specific monoclonal antibodies may be covalently complexed to bacterial or plant toxins, such as diphtheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate RPTPσ expressing cells.

For the production of antibodies, various host animals may be immunized by injection with the RPTPσ protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to RPTPσ may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946, 778) can be adapted to produce RPTPσ-specific single chain antibodies.

Antibody fragments which contain specific binding sites of RPTPσ may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to RPTPσ.

5.5. Uses of RPTPσ Coding Sequence

The RPTPσ coding sequence may be used for diagnostic purposes for detection of RPTPσ expression. Included in the scope of the invention are oligoribonucleotide sequences, that include antisense RNA and DNA molecules and ribozymes that function to inhibit translation of RPTPσ. In addition, mutated forms of RPTPσ, having a dominant negative effect, may be expressed in targeted cell populations to inhibit the activity of endogenously expressed wild-type RPTPσ. Such mutated forms of RPTPσ may include, for example, molecules that compete for RPTPσ ligands, thus inhibiting an RPTPσ-induced signal transduction event from occurring.

5.6 Use of RPTPσ Coding Sequence in Diagnostics and Therapeutics

The RPTPσ DNA may have a number of uses for the diagnosis of diseases resulting from aberrant expression of RPTPσ. For example, the RPTPσ DNA sequence may be used in hybridization assays of biopsies or autopsies to diagnose abnormalities, such as the presence of neuroblastomas, of RPTPσ expression; e.g., Southern or Northern analysis, including in situ hybridization assays.

The RPTPσ cDNA may be used as a probe to detect the expression of the RPTPσ mRNA. In a specific example described herein, in the Working Example presented below in Section 7, the expression of RPTPσ mRNA in rat tissues was analyzed. Briefly, rat RPTPσ is highly expressed in the brain as a 5.7 kb transcript. Rat RPTPσ is also expressed in the lung and intestine as a 6.9 kb transcript but at significantly lower level. Further, RPTPσ is expressed in anatomically distinct regions of rat brain and its expression is developmentally regulated. In situ hybridization studies confirm that RPTPσ is localized predominantly in the nervous system and can be detected in the rat as early as embryonic day 12 (E12). During embryonic development, RPTPσ is expressed extensively in the central and peripheral nervous systems, including the trigeminal and dorsal root ganglia as well as retina. In adult rat brain, expression is restricted primarily to the olfactory tubercle, cerebellum, and hippocampus. Within the latter structure, RPTPσ is present in the pyramidal cell layer and the granular layer of dentate gyrus.

Also within the scope of the invention are oligoribonucleotide sequences, that include anti-sense RNA and DNA molecules and ribozymes that function to inhibit the translation of RPTPσ mRNA. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the RPTPσ nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of RPTPσ RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These-include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half—life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

5.7 Use of RPTPσ or Ligands

Depending on the individual molecule and the cellular environment in which the molecule is found, some RPTPσ molecules may become activated upon extracellular ligand binding, and others may become inactivated (the activity referred to here being RPTPσ hosphatase activity). Ligand binding to RPTPσ molecules may affect a variety of cellular processes. Such processes may include, but are not limited to, normal cellular functions such as differentiation, metabolism, and cell cycle control; cellular behavior, such as motility and contact inhibition; in addition to abnormal or potentially deleterious processes such as virus-receptor interactions, inflammation, and cellular transformation to a cancerous state.

As demonstrated in the Working Example presented., below, in Section 7, RPTPσ mRNA is predominantly expressed in neuronal tissue. This neuronal expression is developmentally regulated, with the first RPTPσ mRNA transcripts being detectable during embryogenesis. In addition, the neuronal expression of RPTPσ is spatially restricted, with transcripts being expressed in specific regions of neuronal tissue. Thus, cellular processes, such as those described above, may be involved in the regulation of neuronal development, differentiation, and metabolism. The methods described below, therefore, may be useful in the identification of compounds capable of treating RPTPσ-related neuronal disorders, such as, potentially, neuroblastomas.

RPTPσ, its equivalent derivatives, and analogs, and ligands of such molecules may be used as drugs that can modulate the cellular processes under the control of RPTPσ. In addition, methods are presented below for the identification of compounds that affect RPTPσ activity, and such compounds may also be used as drugs that can modulate one or more of the cellular processes mentioned above.

RPTPσ or RPTPσ derivatives or analogs, or ligands of such molecules may be used directly to modulate processes such as those mentioned above. For example, soluble RPTPσ may be produced and administered, using techniques well known to those skilled in the art, that would be capable of competing with endogenous transmembrane RPTPσ molecules for available ligands, thus reducing or inhibiting ligand binding to endogenous RPTPσ. Such soluble RPTPσ molecules may consist of all or part of the extracellular domain of the RPTPσ molecule, i.e., may contain all or part of from about amino acid 24 to about amino acid 850 (before signal sequence cleavage) of the RPTPσ protein. The effect of such a procedure would be to activate, reduce or block (depending on what the usual effect of ligand binding to the particular native RPTPσ molecule in question is) the biological activity of the native RPTPσ molecule. The RPTPσ molecules used here may include the entire molecule or, alternatively, only the RPTPσ extracellular domain, or a part of the RPTPσ extracellular domain thereof.

In addition, RPTPσ ligands may be administered, again, using techniques well known to those in the art. (Methods for the identification of such ligands are presented below.) Such administration would lead to a greater than normal number of transmembrane RPTPσ being bound by ligand, potentially causing an amplification of the ligand-bound state within cells exhibiting RPTPσ. Alternatively, the administered ligand may be composed of a modified form of said ligand such that receptor binding may still occur, but the normal result of such binding (receptor activation or inactivation, as the case may be) does not occur. A ligand with such a design would act in much the same way that administration of soluble RPTPσ would, in that both procedures would have the final effect of reducing the number of functionally bound RPTPσ transmembrane molecules, therefore lowering or blocking the normal extracellular signal being transduced into the RPTPσ-exhibiting cell via normal ligand binding to transmembrane RPTPσ.

Depending on the specific conditions being treated, agents may be formulated and administered systemically or locally. Techniques for formulation and administration may be found in "Remington's Pharmaceutical Sciences," 18th Edition, Mack Publishing Co., Easton, Pa., 1990. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

RPTPσ may also be used to screen for additional molecules that can act to modulate the activity of cellular processes such as those described above. For example, compounds that bind to RPTPσ may be identified. Such molecules may include, but are not limited to, natural ligands of RPTPσ, other proteins or glycoproteins, or small synthetic molecules. One method that may be pursued in the isolation of such RPTPσ-binding molecules would include the attachment of RPTPσ molecules to a solid matrix, such as agarose or plastic beads, microtiter wells, or petri dishes, and the subsequent incubation of attached RPTPσ molecules in the presence of a potential RPTPσ-binding compound or compounds. After incubation, unbound compounds are washed away, and the RPTP-bound compounds are recovered. In this procedure, large numbers of types of molecules may be simultaneously screened for RPTPσ-binding activity. Bound molecules could be eluted from the RPTPσ molecules by, for example, competing them away from the RPTPσ molecules with the addition of excess ligand, or by changing the pH and/or ionic environment of the bound molecules.

The effect of a compound on the phosphatase activity of RPTPσ molecules can also be determined. Such a compound may, for example, be one isolated using a procedure such as the binding technique described above. One method that may be utilized for determining the effects of a compound on RPTPσ phosphatase activity may involve exposing such a compound to a preparation of cultured cells that express the RPTPσ of the invention, and subsequently measuring the phosphatase activity of the culture. The compound of interest may be introduced to the cells, for example, by addition of the compound to the tissue culture medium. The phosphatase activity of the cells within the tissue culture preparation may be determined by measuring the level of cellular phosphotyrosine within the culture, using method that are well known in the art (Honegger et al., 1987, Cell 51:199–209; Margolis et al., 1989, Cell 57:1101–1107). To properly determine the effects of addition of the compound, the cellular phosphotyrosine levels of the same type of tissue culture preparation that has not been exposed to this compound must also be measured, and the two levels must then be compared. For example, RPTPσ molecules may be incorporated into apparatuses including but not limited to affinity columns such that large numbers of molecules may be screened quickly by being applied to said apparatuses. Those molecules with an affinity for RPTPσ will be bound. Such binding will also bring about a partial purification of the molecules of interest. In order to continue the purification process, the bound molecules should be eluted off the above described apparatuses, for example by competing them away from the RPTPσ with excess ligand, and the process would then be repeated until the molecule of interest is purified to the extent necessary.

Having now generally described the invention, the same will be more readily understood through reference to the following example which is provided by way of illustration, and is not intended to be limiting of the present invention, unless specified.

6. EXAMPLE: ISOLATION AND ANALYSIS OF RAT RPTPσ cDNA CLONES 6.1. Isolation Of Novel PTPase Domains From Total RNA OF PC12 Cells By PCR A pair of degenerate oligomers: 5'-GA(T/C)TA(T/C)AT(T/C)AA(T/C)GCI AG(T/C)TT-3' (SEQ ID NO:8) and 5'A(T/C)ICCIGC(A/G)CT(A/G)CA(A/G)TGIAC-3'(SEQ ID NO:10), corresponding to conserved amino acid stretches DYINAS (SEQ ID NO:9) and VHC-SAG (SEQ ID NO:11) of known PTPase domains, was used in the RNAPCR to specifically amplify novel sequences of PTPase domain from 1 μg of PC12 total RNA (following procedures recommended by Perkin Elmer/Cetus). PCR products of expected size (about 450 bp) were isolated by agarose gel electrophoresis, purified and then cloned into a pBluescript vector (Stratagene). The cDNA inserts were sequenced by the dideoxy chain termination method using the Sequenase Version 2.0 Kit. Sequencing of about 100 individual clones led to the identification of three PTPase domains whose predicted sequences were homologous to, but distinct from, corresponding sequences of all known PTPs.

6.2. Library Screening and Isolation of cDNA Clones

The cDNA insert from one of the above PTPase domains, referred to as the σ PTPase domain, was amplified and labelled using a random priming labelling kit. The labelled cDNA insert was then used as a probe to screen a rat brain stem cDNA library (Sambrook, J. et al., *MOLECULAR CLONING: A LABORATORY MANUAL,* 2nd Edition, Cold Spring Harbor Press, Cold Spring Harbor, New York (1989)).

About 600,000 recombinants were screened, from which seventeen positive clones were purified after the first round of screening. The most 5' end of the longest cDNA insert isolated following the first round of screening was used in successive rounds of screening until overlapping cDNA clones that contained the entire coding sequence for RPTPσ were obtained. Both strands of several overlapping cDNA clones were sequenced using a Pharmacia DNA Sequencer.

6.3. Sequence Alignments

All DNA and protein database searches were done with the Genetic Computer Group sequence analysis software package (Devereux et al., *Nucleic Acid Res.* 12:387–396 (1989)). The SwissProt and Gene Bank\European Molecular Biology Laboratory databases were searched with FASTA and TFASTA programs, respectively (Pearson and Lipman, Proc. Natl. Acad. Sci. 85:2444–2448 (1988)). Protein sequences were aligned with the Genetics Computer Group programs, LINEUP, PILEUP, PRETTY and BESTFIT.

6.4. Results and Discussion 6.4.1. Molecular Cloning of the full-length cDNA for RPTPσ

Three cDNA fragments coding for novel PTPase domains were initially identified in the total RNA isolated from PC12 cells by reverse PCR with the primers for the conserved regions of other known PTPs. One of these PTPase domains, termed the σ PTPase domain, was expressed at high levels in the brain and only to a limited extent in the lung and intestine. Based on these observations, a random and oligo-dT primed rat brain stem cDNA library (Clontech Inc.) was screened for the full length cDNA of RPTPσ using the PCR fragment initially cloned from the RNA of PC12 cells.

After three rounds of screening, several overlapping clones were isolated. They were sequenced in both directions. As shown in FIG. 1, the 5.7 kb full length cDNA for RPTPσ was constructed by joining the two longest overlapping clones (H-29 and B-10) at a unique MluI site.

The 5.7 kb cDNA has an open reading frame of 1501 amino acid residues starting from the ATG at bp 833. The ATG was preceded by stop codons in all three reading frames and meets the requirements for the translation initiation site (Kozak, M. (1984) *Nucl. Acid Res.* 12:857–871). There is an 832 bp 5'-untranslated sequence and a 352 bp 3'-untranslated sequence containing a polyA tail.

6.4.2. Characterization of RPTPσ

The deduced amino acid sequence for RPTPσ is shown in FIG. 2(A)–2(G). It contains 23 hydrophobic amino acid residues that may function as a signal peptide (von Heijne, G. (1986) *Nucl. Acid Res.* 14:4683–4691), followed by an 824 amino acid extracellular domain and a 24 hydrophobic amino acids transmembrane domain. The 627 amino acid cytoplasmic region contains two tandem PTPase domains.

The overall sequence of RPTPσ demonstrates a high degree of similarity to rat LAR (Yu et al., supra), having 71% sequence identity within the entire coding region. RPTPσ is also 75% identical to partially sequenced hPTP-δ (Krueger et al., supra).

The extracellular segment of RPTPσ consists of 3 Ig-like domains (residue 33 to 315); Williams, A. F. (1987) *Immunol. Today* 8:298–303) and 5 FNIII-like repeats (residue 320 to 786; Kornblihtt, A. R. et al., (1985) *EMBO J.* 4:1755–1759; Hynes, R. (1985) *Ann. Rev. Cell*

Biol.1:67–90). Search in database revealed significant homology to the extracellular segments of rat LAR (63% identity). Also, the homology between the Ig-like domains of RPTPσ and LAR (75% identity) is greater than that of the FNIII-like repeats (54% identity). There was significant homology also between the FNIII-like repeats of RPTPσ and hPTP-δ. In addition, the extracellular sequence of RPTPσ is homologous to neural cell adhesion molecules in overall structure and sequence. The highest homology was detected with L1 (26% identity) (Moos, M. et al., (1988) Nature 334:701–703), followed by N-CAM (22% identity) (Barthers et al.) and neuroglian (22%) (Bieber, A. J. et al., (1989) Cell 59:447–460). FIG. 3 shows alignment of three Ig domains of RPTPσ to each other and to the first Ig domain of rat LAR and mouse N-CAM, respectively. Within each Ig domain, two cysteines are thought to be involved in intra-domain disulfide binding, are conserved (FIG. 3, asterisks). The alignment of the five FNIII-like repeats of RPTPσ to each other and to the first FNIII-like repeat of rat LAR and type III repeat (domain 7) of human fibronectin is shown in FIG. 4. The fifth repeat of RPTPσ exhibits greater divergence from consensus than other four. Also, the extracellular region of RPTPσ does not contain the RGD sequence that is required for fibronectin binding (Ruoslahti, E. et al. (1986) Cell 44:517–518).

The cytoplasmic segment of RPTPσ, like most receptor tyrosine phosphatases, contains two conserved PTPase domains in tandem. PTPase domain I shows 47% sequence identity with PTPase domain II (FIG. 5). The cysteine residues, which have been implicated to be essential for phosphatase activity, are conserved in both PTPase domains. The overall cytoplasmic segment of RPTPσ has a striking sequence homology to that of rat LAR (84% identity) and hPTP-δ (86% identity). Furthermore, comparison of the cytoplasmic segments of RPTPσ and rat LAR indicates that a higher degree of identity is present between domain II (93%) than domain I (84%). A schematic diagram showing the multiple domain structure of RPTPσ is presented in FIG. 5.

Although RPTPσ is highly homologous to rat LAR, especially in the cytoplasmic region, the diversity of their extracellular domains, particularly in the FN III-type repeats, demonstrates that RPTPσ is a new member of the type II receptor tyrosine phosphatases.

The nucleotide sequence of RPTPσ (SEQ ID NO:1) is shown in FIG. 2(A)–2(G). The complete amino acid sequences of RPTPσ (SEQ ID NO:2) is also shown in FIG. 2(A)–2(G).

A database search revealed that RPTPσ is structurally similar to rat LAR with an overall sequence identity of 71%. Homology among the cytoplasmic domains (84%) is greater than that of the extracellular domains (63%). RPTPσ was mapped to distal chromosome 17 of the mouse, which corresponds in part to human chromosome 6 and 19. Hence, we conclude that RPTPσ is a novel member of the type II receptor tyrosine phosphatases.

Unlike rat LAR which has 6 predicted N-glycosylation sites, no such sites have been found in the extracellular domain of RPTPσ. However, this domain is rich in serine and threonine residues (16%) and likely to provide multiple attachment sites for O-linked glycosylation. Moreover, RPTPO has only five FNIII repeats while LAR contains eight. It is possible that larger alternatively spliced transcript (6.9 kb) encodes a protein containing eight FNIII-like repeats.

Like other type II receptor tyrosine phosphatases, such as PTP-μ, RPTPκ, DLAR and DPTP, the extracellular segment of RPTPσ consists of both Ig-like and FNIII-like repeats. This structural feature also has been identified in neural cell adhesion molecules such as N-CAM, NG-CAM and NR-CAM (Edelman et al., supra; Grumet et al., supra). It has been demonstrated that the extracellular domain, especially the Ig-like repeats of these neural adhesion molecules, is crucial for mediating homophilic and heterophilic binding when expressed in transfected cells (Edelman, G. M. et al. (1987) Proc. Natl. Acad. Sci. USA 84:8502–8505; Mauro, V. P. et al., (1992) J. Cell Biol. 119:191–202). Since there is significant homology among the extracellular domains of RPTPσ and L1, N-CAM and neuroglian (26%, 22% and 22% identity, respectively), it is possible that the extracellular domain of RPTPσ also mediate such binding which, in turn, couples the tyrosine phosphatase activity to some intracellular signalling pathway.

Immunoblot analyses suggest that RPTPσ, like LAR and RPTPκ, undergoes proteolytic processing. Sequence analysis indicate that RPTPσ has several .potential cleavage motifs, such as RK at residues 731–732, RR at 762–763, and RHSR at residues 766–769; all located within the 5th FNIII repeat of the extracellular domain. These sites may serve as specific cleavage signals for proteolytic processing (Barr, P. J. (1991) Cell 68:1–3).

7. EXAMPLE: EXPRESSION AND TISSUE DISTRIBUTION OF RPTPσ

7.1. Methods 7.1.1. RNA Isolation And Northern Blot Analysis

Total RNA was isolated from different tissues of 6 day old rats using RNA isolation kits obtained from Stratagene. Samples containing 20 μg of total RNA were resolved in a formaldehyde/agarose gel (Sambrook et al., supra) and then transferred to Nytran membrane (Schleicher & Schuell). Probes corresponding to different cDNA regions of RPTPσ were amplified by PCR, purified, and labelled using a random priming kit. Hybridization and subsequent washing were carried out essentially as described (Ausubel, F. M. et al., Current Protocols in Molecular Biology, Wiley Interscience, New York, 1989 ) with an additional wash carried out in 0.1×SSC and 0.1% SDS at 60° C. for 15 min.

7.1.2. In situ Hybridization

Probe-1 had the following nucleotide sequence (5' to 3'): TAGACCACAATGGAACCATCGTTGTCAG-GCTTTGGGGCGACACTAGGCTT (SEQ ID NO:12). Probe-1 was synthesized in an Applied Biosystems 380A DNA Synthesizer and then purified. Probe-1 is antisense and complementary to the cDNA of RPTPσ from nucleotide 2918 to 2967; a region that encodes amino acid stretch KPSVAPKPDNDGSIVVY (SEQ ID NO:3) from residue 694 to 710. This probe was chosen because it is least homologous to the corresponding sequences in rLAR and hPTP-δ.

Probe-1 was labelled at 3'-end with [α-$^{35}$S]dATP using a terminal deoxynucleotidyl transferase kit and was then purified by Sephadex G-25 column chromatography. The specific activities of the labelled probe ranged from 1 to 4×10$^8$ cpm/μg DNA.

Adult male and timed-pregnant female Sprague-Dawley rats and their litters were used for the study. The day of successful copulation was determined by the presence of sperm in vaginal smears and recorded as embryonic day 0 (E0). The day of birth was considered postnatal day 0 (PO). Whole bodies of E12 embryos were fixed in 4% paraformaldehyde in 0.1M sodium phosphate, pH 7.4, for 4 hours followed by overnight infiltration with 15% sucrose in 0.1M sodium phosphate, pH 7.4. Adult rats were sacrificed by decapitation and then the brains were rapidly removed and frozen on dry ice. 20 μm sections obtained with a cryostat microtome were postfixed for 30 min, and then washed three times in 0.1M sodium phosphate, pH 7.4. The sections were then dehydrated and stored at −20° C.

Prehybridization and hybridization were carried out as described elsewhere (Barnea et al., supra; Levy, J. B. et al., (1993) J. Biol. Chem. in press). Sections were mounted on the slides and incubated with 1×10⁶ CPM labelled probe-1 in 10 mM DTT. The specificity of hybridization was determined by incubating an adjacent section with labelled probe-1 in the presence of a 70 fold excess of unlabelled probe-1. The slides were washed twice in 2×SSC at room temperature (30 min), 1×SSC at 50° C. (30 min), 0.5×SSC at 50° C. (30 min) and finally in 0.5×SSC at room temperature (10 min). Sections were dehydrated and exposed to X-Omat film for 10 days.

7.1.3. Generation of Antibodies Against RPTPσ-GST Fusion Proteins and Peptide Derived from RPTPσ

The cDNA fragments coding for amino acid 100 to 510, 512 to 835 and 964 to 1501, respectively, were amplified by PCR and subcloned into a pGEX expression vector (Pharmacia) to construct corresponding recombinant plasmids (pGEX-EX,PGEX-FNIII, pGEX-CY respectively).

After induction with IPTG, the insoluble GST fusion proteins produced from each of the above constructs were isolated by SDS-PAGE. Two rabbits were immunized with the fusion protein to produce polyclonal antisera against RPTPσ. The polyclonal antibodies against amino acid 512 to 835 was designated as FNIII antibodies.

Three peptides, HAI-1,2 and 3, corresponding amino acid 795 to 809, 1488 to 1501 and 27 to 41 of RPTP-σ, respectively, were synthesized chemically and conjugated with carrier protein, KLH. Two rabbits were immunized with each fusion protein conjugate to produce polyclonal antisera against the peptides of RPTP-σ.

7.1.4. Transfection, Immunoprecipitation and Immunoblot Analyses

A cDNA insert containing the entire open reading frame of RPTPσ was subcloned into an eukaryotic expression vector to generate RKSigma and RKSigmaR, in which the cDNA insert was oriented in the sense or antisense direction, respectively.

Human embryonic kidney 293 cells, grown to 20% confluence on fibronectin coated dishes, were transiently transfected with appropriate plasmids by the calcium phosphate precipitation method (Ausubel et al., supra). The transfected cells were harvested after 48 hrs and lysed in RIPA buffer (137 mM NaCl, 10% glycerol, 1% Triton X-100, 0.5% deoxycholate, 0.1% SDS, 2 mM EDTA, 20 mM Tris, pH 7.3) containing proteinase inhibitors aprotinin and leupeptin (1 μg/ml) and PMSF (100 μg/ml)]. After centrifugation (15,000g, 15 min at 4° C.), the supernatants were analyzed by either (1) immunoprecipitation with FNIII Ab followed by immunoblot analysis or (2) directly by immunoblot analysis. The proteins resolved by SDS-PAGE were transferred onto Nytran membranes, immunoprobed with FNIII Ab, and visualized with $^{125}$I-Protein-A after exposure to X-ray film.

7.2. Results and Discussion

7.2.1. Distribution of RPTPσ mRNA

Northern blot analyses of total RNA isolated from various rat tissues (6 days old) are presented in FIG. 6. The blot depicted in this figure was probed with a cDNA fragment coding for amino acid residues 408 to 521 of RPTPσ. Identical results were obtained with cDNA probe specific for a cytoplasmic segment of RPTPσ.

There are three RPTPσ transcripts of 5.7, 6.9 and 8.5 kb. The 5.7 kb transcript, the most abundant species, and the 8.5 kb transcript were expressed exclusively in brain. The 6.9 kb transcript was expressed to a significantly lesser extent in brain and also in lung and intestine. The cDNA that was sequenced and described herein probably corresponded to the 5.7 kb mRNA.

7.2.2. In Situ Hybridization

Since RPTPσ is highly expressed in the brain as detected by Northern blot analysis, its expression at specific sites within whole embryos and adult rat brain was then identified by in situ hybridization. Using labelled probe-1, an antisense oligomer, the expression of RPTPσ was detected in brain, spinal cord, and dorsal root ganglia as early as embryonic day E12 (FIG. 7(A)). No apparent expression was detected in other tissues. Hybridization signals were specific since they were completely chased by a 70-fold excess of unlabelled probe-1 (FIG. 7(B)). In addition, a relatively low level of the expression of RPTPσ was detected in the lung at embryonic day 18 (El8) and the intensity of RPTPσ expression overall gradually decreased during embryonic development.

In the adult rat brain, expression of RPTPσ was confined to specific regions of the brain that included the olfactory bulb, cerebellum and hippocampus (FIG. 7(C)). Within the latter structure, the pyramidal cell layer and granular layer of dentate gyrus were labelled specifically (FIGS. 7(C), 7(D)).

7.2.3. Transient Expression of RPTPσ

Human embryonic kidney 293 cells were transfected transiently with a mammalian expression vector that directs the synthesis of RPTPσ in order to investigate its biochemical properties. The transfected cells were lysed in REPA buffer and the supernatants then subjected to immunoprecipitation with polyclonal FNIII Ab. This was followed by immunoblot analysis using the same antibodies. The results shown in FIG. 8, panel A, revealed that FNIII Ab can specifically detect a protein of 200 kDa in supernatants from cells transfected with a plasmid containing RPTPσ cDNA (RKSigma) (FIG. 8, panel A, lane 1) but not from those transfected with a plasmid containing control DNA (RKSigmaR) (FIG. 8 panel A, lane 2). No band corresponding to the 200 kDa protein was detected in control immunoprecipitation experiments using preimmune serum.

The apparent molecular weight of the expressed protein after SDS-PAGE is in good agreement with the expected size for RPTPσ. The bands detected in lane 2 of FIG. 8, panels A and B, were non-specific since they were also observed after incubation with preimmune serum.

Several members of the type II tyrosine phosphatases, such as LAR (Streuli, M. et al., (1992) *EMBO J.* 11:879–907) and PTP-κ (Jiang et al., supra), undergo proteolytic processing after synthesis. To investigate whether similar processing occurs with RPTPσ, the supernatants of lysates from the transfected cells were subjected directly to immunoblot analysis using FNIII Ab or preimmune serum. The results presented in FIG. 8, panel B show that in addition to the 200 kDa protein previously identified, an additional protein with an apparent molecular weight of 100 kDa was detected in lysates of cells transfected with plasmid RKSigma (lane 1), but not with RKSigmaR (lane 2). No such bands at 200 and 100 kDa were detected with preimmune serum.

Identical results also were obtained in immunoblot experiments with the supernatants from lysates of transfected COS-1 cells.

These results suggest that RPTPσ also undergoes proteolytic processing and the 100 kD protein may represent a cleavage product.

Numerous studies have indicated that CD45 plays a crucial role in coupling the T cell antigen receptor to a intracellular signaling pathway (Trowbridge, I. S. (1991) *J. Biol. Chem.* 266:23517–23520; Shaw, A. et al. (1991) *Curr. Opin. Cell Biol.* 3:862–868; Desai, D. V. et al., (1993) *Cell* 73:1–20). Experiments have suggested CD45 can activate Lck or fyn protein tyrosine kinases by dephosphorylation at inhibiting sites at the carboxy-terminus (Shiroo, M. et al., (1992) *EMBO J.* (1992) 11:4887–4897; Mustelin, T. et al., (1989) *Proc. Natl. Acad. Sci. USA* 86:6302–6306). In the mammalian nervous system several tyrosine kinases such as c-yes (Sudol, M. et al., (1889) *Mol. Cell. Biol.* 9:4545–4549), and the neuron-specific form of c-src (Ross, C. A. et al., (1988) *Proc. Natl. Acad. Sci. USA* 85:9831–9835) have been shown to be expressed at high levels in the brain. Moreover, protein tyrosine kinase inhibitors have been shown to block long-term potentiation in the hippocampus (O'Dell, T. J. et al., (1991) *Nature* 353:558–560). Furthermore, it has been demonstrated that several receptor tyrosine kinases, such as NGF and FGF receptors (Chao, M. V. (1992) *Neuron* 9:583–593), play a central role in neural development. The molecular cloning of RPTPσ, which is expressed primarily in both the central and peripheral nervous systems of embryo and adults, will assist in the determination of the role of tyrosine phosphatases in mammalian neurogenesis and maintenance.

8. EXAMPLE: CHROMOSOMAL LOCALIZATION OF THE MURINE RPTPσ GENE

Inbred and recombinant inbred (RI) mice were obtained from The Jackson Laboratory (Bar Harbor, Me.). Genomic DNA was isolated from liver, digested with restriction enzyme TaqI, and then analyzed by Southern blotting with probe PGEX-FNIII (see above) as described previously (D'Eustachio, P. et al., (1987) *Immunogenetics* 26:339–343).

To establish genetic linkages, the distribution patterns observed for RPTPσ in the RI strains were compared to approximately 1360 other markers maintained in a database at New York University by Dr. P. D'Eustachio. Significance of matches was assessed using the BAYLOC algorithm (Blank, R. D. et al., (1988) *Genetics* 120:1073–1083).

When TaqI-digested genomic DNA from various inbred strains was analyzed by Southern blotting using an RPTPσ probe (pGEX-FNIII), two allelic forms of the gene were detected (Table 1A). The pattern of inheritance of these alleles in recombinant inbred strains of mice defined a single genetic locus (Table 1B). Comparison of the inheritance pattern for this locus with these previously established for approximately 1360 markers distributed over the entire mouse genome allowed us to map the locus for RPTPσ to distal mouse Chromosome 17.

TABLE I

DNA FRAGMENT LENGTH VARIANT ASSOCIATED WITH THE MOUSE RPTPk GENE

A. Alleles of RPTPσ defined by Southern Blotting
Allele (Size kb)) Strains
a 5.6AKR, 020/A, DBA/2J, C57BL/6J,
C3H/HeJ, BALB/c, NZB/B1NJ,
SM/J, A/J, PL/J
b5.4C57L/J, SWR/J, SJL/J, STS/A,
129/J TABLE I-continued DNA FRAGMENT LENGTH VARIANT ASSOCIATED WITH THE MOUSE RPTPk GENE B. Inheritance of RPTPσ Alleles in Recombinant Inbred
strains
AKXLBXJNX129
   111111 12222 233 11
56789 234567 91458 97812106
LAAAA LAALL AALLL LLL JBN9N
CXSCXJ
     1 1111 1
12345 67890 123413468 95
CSSSS SCCCC CSCSCCJJC CC C. Linkage Relationships Deduced from RI Typing Data
Marker Chr R/N OddsDistance in cM
(95% limits)
H-2178/390.03248 7.4 (2.7–20.1)
C3170/140.00634 -- (<8.9)
Ras12-3170/180.00049 -- (<6.4)
Hprt-2ps171/180.00972 1.5 (0.0–11.6)

(A) Variant DNA fragments in Southern blots of TaqI-digested genomic DNA.
(B) All RI strains were homozygous for one of the progenitor strain alleles of RPTPσ, as indicated by the generic symbols: 9, 129/J-like; A, AKR/J-like; B, C57BL/6J-like; C, BALB/c-like; J, SJL-like; L, C57L/J-like; N, NZB/B1NJ-like; and S, STS/A-like.
(C) The strain distribution pattern for RPTPσ was compared to ones for 436 other markers. All concordances whose odds of chance occurrence are less than 0.05 are shown. For each such match, the Marker name and chromosomal location (Chr) are shown, together with the observed recombination fraction (R/N), Odds of observing that fraction or a smaller one by chance (Blank, R.D. et al., (1988) Genetics 120:1073–1083), and, conditional on the existence of linkage, the estimated distance in cM between the two loci and the 95% binomial confidence limits for that estimate.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An isolated polypeptide that is a naturally occurring receptor-type protein tyrosine phosphatase-a protein having (i) the amino acid sequence SEQ ID NO: 3; or (ii) an amino acid sequence encoded by a nucleic acid molecule that hybridizes under stringent conditions to a nucleic acid molecule comprising the nucleotide sequence of the complement of SEQ ID NO: 2.

2. A polypeptide having an amino acid sequence: 1–23, 33–124, 136–225, 233–315, 320–411, 415–510, 513–603, 604–689, 693–786, 851–874, 875–963, 964–1207, 1254–1501, 100–510, 512–835 or 964–1501 of SEQ ID NO:3.

3. A polypeptide having the amino acid sequence of claim 1 lacking one or more amino acid residues of one or more of the following regions shown in SEQ ID NO: 3: 1–23, 33–124, 136–225, 233–315, 320–411, 415–510, 513–603, 604–689, 693–786, 851–874, 875–963, 964–1207, 1254–1501, 100–510, 512–835, or 964–1501.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note= "Xaa = Isoleucine or Valine"

( i x ) FEATURE:
        ( A ) NAME/KEY: Modified-site
        ( B ) LOCATION: 4
        ( D ) OTHER INFORMATION: /label=Xaa
            / note= "Xaa = any amino acid"

( i x ) FEATURE:
        ( A ) NAME/KEY: Modified-site
        ( B ) LOCATION: 7
        ( D ) OTHER INFORMATION: /label=Xaa
            / note= "Xaa = any amino acid"

( i x ) FEATURE:
        ( A ) NAME/KEY: Modified-site
        ( B ) LOCATION: 8
        ( D ) OTHER INFORMATION: /label=Xaa
            / note= "Xaa = any amino acid"

( i x ) FEATURE:
        ( A ) NAME/KEY: Modified-site
        ( B ) LOCATION: 10
        ( D ) OTHER INFORMATION: /label=Xaa
            / note= "Xaa = Serine or Threonine"

( x i ) SEQUENCE DESCRIPTION: SEQ ID NO:1:

```
Xaa  His  Cys  Xaa  Ala  Gly  Xaa  Xaa  Arg  Xaa  Gly
 1                   5                        10
```

( 2 ) INFORMATION FOR SEQ ID NO:2:

( i ) SEQUENCE CHARACTERISTICS:
        ( A ) LENGTH: 5690 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 833..5338

( x i ) SEQUENCE DESCRIPTION: SEQ ID NO:2:

```
GGCACGAGCC  AGACACTAGC  TGAAAAGTCA  GGTGACAGAA  ACAATGATTC  AGACTGATCA      60
CATGATTACA  AAGCTGGGGG  CTCCAGCAGG  GCTCCAGGTG  GTCGGGGTGG  ACATCTAAGG     120
AAGCAGTGAC  ATGGGAGGGG  CAAGCACTGG  GCCAGCCTTG  AGCCGCCTGG  ATGACAGAGA     180
CAGAGGATCT  GGTAGCTCCA  GGGATCTCCG  GTCCATGCCT  TACTTGGCCA  GGGGGTTCCT     240
GAAGGACCTG  CCGGCAAACT  TGGCTTTGCT  GCCCAGCTCC  TCCTCGATTC  TAAGGATCTG     300
```

-continued

```
ATTGTACTTG GCCAGGCGCT CAGATCGGCA GGGGGCACCA GTCTTGATCT GCCCAGTGCA      360

GAGCCCCACC ACCAGGTCGG CAATGAAAGT GTCCTCAGTC TCCCCAGATC GATGGGACAC      420

CATGACACCC CAGCCATTGG ACTGGGCCAG CTTACACGCC TGCAGAGACT CGGTCACAGA      480

GCCAATCTGG TTCACTTTGA GCAGGAGGCA GTTGCAGGAC TTTTCGCCTG CAGCCTTGGC      540

GATCCGCTTA GGGTTGGTCA CTGTGAGGTC ATCCCCACC ACCTGGATGC CTGCAGTAGC       600

TGTGAACTTC TGCCAAGCAT CCCAGTCGTC CTGGTCAAAG GGATCTTCAA TGGACACCAC      660

TGGGTAGTCC TTGATGAAGG ACTTGTACAG GTCGGCCAGC TGGTCGGGTG TGATGTACCG      720

GCTGGCATCA TCTGGAGACT TGAAGTCCAG GTCATACTTG CCAGCCCTGT AGAATTCGGA      780

GGCAGCCACA TCCATCCCCC ACCAGGGCGG AGGCTGGAGG CCACTGCCAA GC ATG         835
                                                              Met
                                                               1
```

| | | | | | | | | | | | | | | | | |
|---|---|---|---|---|---|---|---|---|---|---|---|---|---|---|---|---|
| GCG | CCC | ACC | TGG | AGA | CCC | AGC | GTG | GTG | TCT | GTG | GTG | GGT | CCT | GTG | GGG | 883 |
| Ala | Pro | Thr | Trp | Arg | Pro | Ser | Val | Val | Ser | Val | Val | Gly | Pro | Val | Gly | |
| | | | 5 | | | | | 10 | | | | | 15 | | | |
| CTC | TTC | CTT | GTA | CTG | CTG | GCC | AGA | GGG | TGC | TTG | GCT | GAA | GAG | CCA | CCC | 931 |
| Leu | Phe | Leu | Val | Leu | Leu | Ala | Arg | Gly | Cys | Leu | Ala | Glu | Glu | Pro | Pro | |
| | | | | 20 | | | | 25 | | | | | 30 | | | |
| AGA | TTT | ATC | AGA | GAG | CCC | AAG | GAT | CAG | ATT | GGT | GTG | TCA | GGA | GGC | GTG | 979 |
| Arg | Phe | Ile | Arg | Glu | Pro | Lys | Asp | Gln | Ile | Gly | Val | Ser | Gly | Gly | Val | |
| | | 35 | | | | | 40 | | | | | 45 | | | | |
| GCC | TCC | TTC | GTG | TGC | CAG | GCC | ACA | GGT | GAC | CCT | AAG | CCA | CGG | GTG | ACC | 1027 |
| Ala | Ser | Phe | Val | Cys | Gln | Ala | Thr | Gly | Asp | Pro | Lys | Pro | Arg | Val | Thr | |
| 50 | | | | | 55 | | | | | 60 | | | | | 65 | |
| TGG | AAC | AAG | AAG | GGC | AAG | AAA | GTG | AAC | TCA | CAG | CGC | TTT | GAG | ACC | ATT | 1075 |
| Trp | Asn | Lys | Lys | Gly | Lys | Lys | Val | Asn | Ser | Gln | Arg | Phe | Glu | Thr | Ile | |
| | | | 70 | | | | | 75 | | | | | 80 | | | |
| GAC | TTT | GAC | GAG | AGC | TCG | GGG | GCC | GTG | CTG | AGG | ATC | CAG | CCA | CTT | CGG | 1123 |
| Asp | Phe | Asp | Glu | Ser | Ser | Gly | Ala | Val | Leu | Arg | Ile | Gln | Pro | Leu | Arg | |
| | | | | 85 | | | | | 90 | | | | | 95 | | |
| ACA | CCC | CGG | GAT | GAG | AAC | GTG | TAC | GAG | TGT | GTG | GCC | CAG | AAC | TCG | GTG | 1171 |
| Thr | Pro | Arg | Asp | Glu | Asn | Val | Tyr | Glu | Cys | Val | Ala | Gln | Asn | Ser | Val | |
| | | | 100 | | | | | 105 | | | | | 110 | | | |
| GGG | GAG | ATC | ACA | GTT | CAT | GCG | AAG | CTC | ACC | GTC | CTG | CGA | GAG | GAC | CAG | 1219 |
| Gly | Glu | Ile | Thr | Val | His | Ala | Lys | Leu | Thr | Val | Leu | Arg | Glu | Asp | Gln | |
| | 115 | | | | | 120 | | | | | 125 | | | | | |
| CTG | CCT | CCT | GGC | TTC | CCC | AAC | ATT | GAC | ATG | GGC | CCC | CAG | TTG | AAG | GTT | 1267 |
| Leu | Pro | Pro | Gly | Phe | Pro | Asn | Ile | Asp | Met | Gly | Pro | Gln | Leu | Lys | Val | |
| 130 | | | | | 135 | | | | | 140 | | | | | 145 | |
| GTA | GAG | CGC | ACA | CGC | ACA | GCC | ACC | ATG | CTC | TGT | GCT | GCC | AGC | GGA | AAC | 1315 |
| Val | Glu | Arg | Thr | Arg | Thr | Ala | Thr | Met | Leu | Cys | Ala | Ala | Ser | Gly | Asn | |
| | | | | 150 | | | | | 155 | | | | | 160 | | |
| CCT | GAC | CCT | GAG | ATC | ACC | TGG | TTC | AAG | GAC | TTC | CTG | CCT | GTG | GAC | CCC | 1363 |
| Pro | Asp | Pro | Glu | Ile | Thr | Trp | Phe | Lys | Asp | Phe | Leu | Pro | Val | Asp | Pro | |
| | | | 165 | | | | | 170 | | | | | 175 | | | |
| AGT | GCC | AGC | AAT | GGG | CGG | ATC | AAG | CAG | CTT | CGG | TCA | GGT | GCC | CTG | CAG | 1411 |
| Ser | Ala | Ser | Asn | Gly | Arg | Ile | Lys | Gln | Leu | Arg | Ser | Gly | Ala | Leu | Gln | |
| | | | 180 | | | | | 185 | | | | | 190 | | | |
| ATT | GAG | AGC | AGC | GAG | GAG | ACA | GAC | CAG | GGC | AAG | TAC | GAG | TGT | GTG | GCC | 1459 |
| Ile | Glu | Ser | Ser | Glu | Glu | Thr | Asp | Gln | Gly | Lys | Tyr | Glu | Cys | Val | Ala | |
| | 195 | | | | | 200 | | | | | 205 | | | | | |
| ACC | AAC | AGC | GCT | GGG | GTG | CGC | TAC | TCA | TCA | CCT | GCC | AAC | CTC | TAC | GTG | 1507 |
| Thr | Asn | Ser | Ala | Gly | Val | Arg | Tyr | Ser | Ser | Pro | Ala | Asn | Leu | Tyr | Val | |
| 210 | | | | 215 | | | | | 220 | | | | | 225 | | |
| CGA | GTC | CGC | CGT | GTG | GCC | CCC | CGC | TTC | TCC | ATC | CTG | CCC | ATG | AGC | CAC | 1555 |
| Arg | Val | Arg | Arg | Val | Ala | Pro | Arg | Phe | Ser | Ile | Leu | Pro | Met | Ser | His | |
| | | | 230 | | | | | 235 | | | | | 240 | | | |

| | | | | | | | | | | | | | | | | |
|---|---|---|---|---|---|---|---|---|---|---|---|---|---|---|---|---|
| GAG | ATC | ATG | CCC | GGT | GGG | AAT | GTG | AAT | ATC | ACT | TGT | GTG | GCT | GTG | GGC | 1603 |
| Glu | Ile | Met | Pro | Gly | Gly | Asn | Val | Asn | Ile | Thr | Cys | Val | Ala | Val | Gly | |
| | | | 245 | | | | 250 | | | | | | 255 | | | |
| TCA | CCC | ATG | CCC | TAC | GTG | AAG | TGG | ATG | CAG | GGG | GCA | GAG | GAC | CTG | ACG | 1651 |
| Ser | Pro | Met | Pro | Tyr | Val | Lys | Trp | Met | Gln | Gly | Ala | Glu | Asp | Leu | Thr | |
| | | 260 | | | | | 265 | | | | | 270 | | | | |
| CCT | GAG | GAT | GAC | ATG | CCC | GTG | GGT | CGG | AAT | GTC | CTC | GAA | CTC | ACG | GAT | 1699 |
| Pro | Glu | Asp | Asp | Met | Pro | Val | Gly | Arg | Asn | Val | Leu | Glu | Leu | Thr | Asp | |
| | 275 | | | | | 280 | | | | | 285 | | | | | |
| GTC | AAA | GAC | TCA | GCC | AAC | TAT | ACT | TGT | GTG | GCC | ATG | TCC | AGC | CTG | GGA | 1747 |
| Val | Lys | Asp | Ser | Ala | Asn | Tyr | Thr | Cys | Val | Ala | Met | Ser | Ser | Leu | Gly | |
| 290 | | | | | 295 | | | | | 300 | | | | | 305 | |
| GTG | ATC | GAG | GCC | GTT | GCT | CAG | ATC | ACT | GTA | AAA | TCT | CTC | CCC | AAA | GCC | 1795 |
| Val | Ile | Glu | Ala | Val | Ala | Gln | Ile | Thr | Val | Lys | Ser | Leu | Pro | Lys | Ala | |
| | | | | 310 | | | | | 315 | | | | | 320 | | |
| CCT | GGG | ACT | CCC | GTG | GTG | ACG | GAG | AAC | ACT | GCT | ACC | AGT | ATC | ACT | GTC | 1843 |
| Pro | Gly | Thr | Pro | Val | Val | Thr | Glu | Asn | Thr | Ala | Thr | Ser | Ile | Thr | Val | |
| | | | 325 | | | | 330 | | | | | 335 | | | | |
| ACA | TGG | GAC | TCA | GGC | AAT | CCT | GAC | CCT | GTG | TCC | TAC | TAC | GTA | ATT | GAG | 1891 |
| Thr | Trp | Asp | Ser | Gly | Asn | Pro | Asp | Pro | Val | Ser | Tyr | Tyr | Val | Ile | Glu | |
| | | 340 | | | | | 345 | | | | | 350 | | | | |
| TAT | AAA | TCC | AAA | AGC | CAG | GAT | GGG | CCG | TAT | CAG | ATC | AAA | GAA | GAC | ATC | 1939 |
| Tyr | Lys | Ser | Lys | Ser | Gln | Asp | Gly | Pro | Tyr | Gln | Ile | Lys | Glu | Asp | Ile | |
| | 355 | | | | | 360 | | | | | 365 | | | | | |
| ACC | ACC | ACG | CGC | TAC | AGC | ATC | GGC | GGC | CTG | AGC | CCC | AAC | TCT | GAG | TAT | 1987 |
| Thr | Thr | Thr | Arg | Tyr | Ser | Ile | Gly | Gly | Leu | Ser | Pro | Asn | Ser | Glu | Tyr | |
| 370 | | | | | 375 | | | | | 380 | | | | | 385 | |
| GAG | ATC | TGG | GTG | TCA | GCT | GTC | AAC | TCC | ATC | GGC | CAG | GGC | CCC | CCC | AGT | 2035 |
| Glu | Ile | Trp | Val | Ser | Ala | Val | Asn | Ser | Ile | Gly | Gln | Gly | Pro | Pro | Ser | |
| | | | | 390 | | | | | 395 | | | | | 400 | | |
| GAG | TCG | GTG | GTG | ACC | CGC | ACA | GGC | GAG | CAG | GCA | CCA | GCC | AGT | GCT | CCC | 2083 |
| Glu | Ser | Val | Val | Thr | Arg | Thr | Gly | Glu | Gln | Ala | Pro | Ala | Ser | Ala | Pro | |
| | | | 405 | | | | 410 | | | | | 415 | | | | |
| AGG | AAT | GTT | CAG | GCG | CGC | ATG | CTC | AGT | GCC | ACC | ACC | ATG | ATT | GTG | CAG | 2131 |
| Arg | Asn | Val | Gln | Ala | Arg | Met | Leu | Ser | Ala | Thr | Thr | Met | Ile | Val | Gln | |
| | | | 420 | | | | 425 | | | | | 430 | | | | |
| TGG | GAG | GAG | CCC | GTG | GAG | CCC | AAT | GGC | CTG | ATC | CGT | GGC | TAC | CGC | GTC | 2179 |
| Trp | Glu | Glu | Pro | Val | Glu | Pro | Asn | Gly | Leu | Ile | Arg | Gly | Tyr | Arg | Val | |
| | 435 | | | | | 440 | | | | | 445 | | | | | |
| TAC | TAC | ACC | ATG | GAG | CCC | GAG | CAT | CCG | GTG | GGC | AAC | TGG | CAG | AAG | CAC | 2227 |
| Tyr | Tyr | Thr | Met | Glu | Pro | Glu | His | Pro | Val | Gly | Asn | Trp | Gln | Lys | His | |
| 450 | | | | | 455 | | | | | 460 | | | | | 465 | |
| AAT | GTG | GAC | GAC | AGT | CTT | CTG | ACC | ACT | GTG | GGC | AGC | CTG | CTA | GAG | GAT | 2275 |
| Asn | Val | Asp | Asp | Ser | Leu | Leu | Thr | Thr | Val | Gly | Ser | Leu | Leu | Glu | Asp | |
| | | | | 470 | | | | | 475 | | | | | 480 | | |
| GAG | ACC | TAC | ACT | GTG | AGA | GTG | CTC | GCC | TTC | ACA | TCG | GTG | GGC | GAT | GGG | 2323 |
| Glu | Thr | Tyr | Thr | Val | Arg | Val | Leu | Ala | Phe | Thr | Ser | Val | Gly | Asp | Gly | |
| | | | 485 | | | | 490 | | | | | 495 | | | | |
| CCA | CTG | TCA | GAC | CCC | ATC | CAG | GTC | AAG | ACC | CAG | CAG | GGA | GTG | CCC | GGC | 2371 |
| Pro | Leu | Ser | Asp | Pro | Ile | Gln | Val | Lys | Thr | Gln | Gln | Gly | Val | Pro | Gly | |
| | | 500 | | | | | 505 | | | | | 510 | | | | |
| CAG | CCC | ATG | AAC | TTG | CGG | GCT | GAG | GCC | AAG | TCA | GAG | ACC | AGC | ATT | GGG | 2419 |
| Gln | Pro | Met | Asn | Leu | Arg | Ala | Glu | Ala | Lys | Ser | Glu | Thr | Ser | Ile | Gly | |
| | 515 | | | | | 520 | | | | | 525 | | | | | |
| CTC | TCG | TGG | AGT | GCA | CCA | CGG | CAG | GAG | AGT | GTC | ATT | AAG | TAT | GAA | CTG | 2467 |
| Leu | Ser | Trp | Ser | Ala | Pro | Arg | Gln | Glu | Ser | Val | Ile | Lys | Tyr | Glu | Leu | |
| 530 | | | | | 535 | | | | | 540 | | | | | 545 | |
| CTC | TTC | CGG | GAG | GGC | GAC | CGA | GGC | CGA | GAG | GTG | GGG | CGA | ACC | TTC | GAC | 2515 |
| Leu | Phe | Arg | Glu | Gly | Asp | Arg | Gly | Arg | Glu | Val | Gly | Arg | Thr | Phe | Asp | |
| | | | | 550 | | | | | 555 | | | | | 560 | | |

-continued

| | | | | | | | | | | | | | | | | |
|---|---|---|---|---|---|---|---|---|---|---|---|---|---|---|---|---|
| CCA | ACC | ACA | GCC | TTT | GTG | GTG | GAG | GAC | CTC | AAG | CCC | AAT | ACG | GAG | TAC | 2563 |
| Pro | Thr | Thr | Ala | Phe | Val | Val | Glu | Asp | Leu | Lys | Pro | Asn | Thr | Glu | Tyr | |
| | | | 565 | | | | 570 | | | | | 575 | | | | |
| GCG | TTC | CGG | CTG | GCG | GCT | CGC | TCG | CCG | CAG | GGC | CTG | GGC | GCC | TTC | ACC | 2611 |
| Ala | Phe | Arg | Leu | Ala | Ala | Arg | Ser | Pro | Gln | Gly | Leu | Gly | Ala | Phe | Thr | |
| | | 580 | | | | | 585 | | | | | 590 | | | | |
| GCG | GTT | GTG | CGC | CAG | CGC | ACA | CTG | CAG | GCC | ATC | TCC | CCC | AAG | AAC | TTC | 2659 |
| Ala | Val | Val | Arg | Gln | Arg | Thr | Leu | Gln | Ala | Ile | Ser | Pro | Lys | Asn | Phe | |
| | 595 | | | | | 600 | | | | | 605 | | | | | |
| AAG | GTG | AAG | ATG | ATC | ATG | AAA | ACT | TCA | GTG | CTG | CTA | AGC | TGG | GAG | TTC | 2707 |
| Lys | Val | Lys | Met | Ile | Met | Lys | Thr | Ser | Val | Leu | Leu | Ser | Trp | Glu | Phe | |
| 610 | | | | | 615 | | | | 620 | | | | | | 625 | |
| CCT | GAC | AAC | TAT | AAC | TCA | CCC | ACG | CCC | TAC | AAG | ATC | CAG | TAC | AAT | GGA | 2755 |
| Pro | Asp | Asn | Tyr | Asn | Ser | Pro | Thr | Pro | Tyr | Lys | Ile | Gln | Tyr | Asn | Gly | |
| | | | | 630 | | | | | 635 | | | | | 640 | | |
| CTC | ACA | CTG | GAC | GTG | GAT | GGC | CGC | ACT | ACC | AAG | AAG | CTG | ATC | ACG | CAC | 2803 |
| Leu | Thr | Leu | Asp | Val | Asp | Gly | Arg | Thr | Thr | Lys | Lys | Leu | Ile | Thr | His | |
| | | | 645 | | | | 650 | | | | | 655 | | | | |
| CTC | AAG | CCA | CAC | ACC | TTC | TAT | AAC | TTC | GTG | CTC | ACC | AAC | CGT | GGC | AGC | 2851 |
| Leu | Lys | Pro | His | Thr | Phe | Tyr | Asn | Phe | Val | Leu | Thr | Asn | Arg | Gly | Ser | |
| | | 660 | | | | | 665 | | | | | 670 | | | | |
| AGC | CTG | GGA | GGC | CTG | CAG | CAG | ACG | GTC | ACC | GCC | AGG | ACC | GCC | TTC | AAC | 2899 |
| Ser | Leu | Gly | Gly | Leu | Gln | Gln | Thr | Val | Thr | Ala | Arg | Thr | Ala | Phe | Asn | |
| | 675 | | | | | 680 | | | | | 685 | | | | | |
| ATG | CTC | AGT | GGC | AAG | CCT | AGT | GTC | GCC | CCA | AAG | CCT | GAC | AAC | GAT | GGT | 2947 |
| Met | Leu | Ser | Gly | Lys | Pro | Ser | Val | Ala | Pro | Lys | Pro | Asp | Asn | Asp | Gly | |
| 690 | | | | | 695 | | | | 700 | | | | | | 705 | |
| TCC | ATT | GTG | GTC | TAC | CTG | CCT | GAT | GGC | CAG | AGT | CCC | GTG | ACA | GTG | CAG | 2995 |
| Ser | Ile | Val | Val | Tyr | Leu | Pro | Asp | Gly | Gln | Ser | Pro | Val | Thr | Val | Gln | |
| | | | | 710 | | | | | 715 | | | | | 720 | | |
| AAC | TAC | TTC | ATT | GTG | ATG | GTC | CCA | CTT | CGG | AAG | TCT | CGT | GGT | GGC | CAG | 3043 |
| Asn | Tyr | Phe | Ile | Val | Met | Val | Pro | Leu | Arg | Lys | Ser | Arg | Gly | Gly | Gln | |
| | | | 725 | | | | | 730 | | | | | 735 | | | |
| TTC | CCT | ATC | CTA | CTA | GGT | AGT | CCA | GAG | GAC | ATG | GAT | CTG | GAG | GAG | CTC | 3091 |
| Phe | Pro | Ile | Leu | Leu | Gly | Ser | Pro | Glu | Asp | Met | Asp | Leu | Glu | Glu | Leu | |
| | | | 740 | | | | 745 | | | | | 750 | | | | |
| ATC | CAG | GAC | CTC | TCC | CGG | CTG | CAG | AGG | CGC | AGC | CTG | CGC | CAC | TCA | AGA | 3139 |
| Ile | Gln | Asp | Leu | Ser | Arg | Leu | Gln | Arg | Arg | Ser | Leu | Arg | His | Ser | Arg | |
| | 755 | | | | | 760 | | | | | 765 | | | | | |
| CAG | CTG | GAG | GTG | CCT | CGG | CCT | TAC | ATC | GCC | GCT | CGG | TTC | TCC | ATC | CTG | 3187 |
| Gln | Leu | Glu | Val | Pro | Arg | Pro | Tyr | Ile | Ala | Ala | Arg | Phe | Ser | Ile | Leu | |
| 770 | | | | | 775 | | | | | 780 | | | | | 785 | |
| CCA | GCT | GTC | TTC | CAT | CCT | GGG | AAC | CAG | AAG | CAA | TAT | GGT | GGC | TTT | GAC | 3235 |
| Pro | Ala | Val | Phe | His | Pro | Gly | Asn | Gln | Lys | Gln | Tyr | Gly | Gly | Phe | Asp | |
| | | | | 790 | | | | | 795 | | | | | 800 | | |
| AAC | AGG | GGC | TTG | GAG | CCA | GGC | CAC | CGT | TAT | GTC | CTC | TTT | GTA | CTT | GCT | 3283 |
| Asn | Arg | Gly | Leu | Glu | Pro | Gly | His | Arg | Tyr | Val | Leu | Phe | Val | Leu | Ala | |
| | | | | 805 | | | | 810 | | | | | 815 | | | |
| GTG | CTG | CAG | AAG | AAT | GAG | CCT | ACA | TTT | GCA | GCC | AGT | CCC | TTC | TCA | GAC | 3331 |
| Val | Leu | Gln | Lys | Asn | Glu | Pro | Thr | Phe | Ala | Ala | Ser | Pro | Phe | Ser | Asp | |
| | | 820 | | | | | 825 | | | | | 830 | | | | |
| CCC | TTC | CAA | CTG | GAC | AAC | CCA | GAC | CCG | CAG | CCC | ATT | GTG | GAT | GGC | GAG | 3379 |
| Pro | Phe | Gln | Leu | Asp | Asn | Pro | Asp | Pro | Gln | Pro | Ile | Val | Asp | Gly | Glu | |
| 835 | | | | | | 840 | | | | | 845 | | | | | |
| GAG | GGC | CTC | ATC | TGG | GTG | ATC | GGG | CCC | GTG | CTG | GCC | GTG | GTC | TTC | ATC | 3427 |
| Glu | Gly | Leu | Ile | Trp | Val | Ile | Gly | Pro | Val | Leu | Ala | Val | Val | Phe | Ile | |
| 850 | | | | | 855 | | | | | 860 | | | | | 865 | |
| ATC | TGC | ATC | GTA | ATT | GCC | ATC | CTG | CTG | TAC | AAG | AAC | AAG | CCT | GAC | AGC | 3475 |
| Ile | Cys | Ile | Val | Ile | Ala | Ile | Leu | Leu | Tyr | Lys | Asn | Lys | Pro | Asp | Ser | |
| | | | | 870 | | | | | 875 | | | | | 880 | | |

-continued

| | | | | | | | | | | | | | | | | |
|---|---|---|---|---|---|---|---|---|---|---|---|---|---|---|---|---|
| AAA | CGC | AAG | GAC | TCA | GAG | CCC | CGC | ACC | AAA | TGC | TTA | TTG | AAC | AAT | GCA | 3523 |
| Lys | Arg | Lys | Asp | Ser | Glu | Pro | Arg | Thr | Lys | Cys | Leu | Leu | Asn | Asn | Ala | |
| | | | 885 | | | | 890 | | | | | 895 | | | | |
| GAC | CTC | GCC | CCC | CAT | CAC | CCC | AAG | GAC | CCT | GTG | GAA | ATG | CGA | CGT | ATC | 3571 |
| Asp | Leu | Ala | Pro | His | His | Pro | Lys | Asp | Pro | Val | Glu | Met | Arg | Arg | Ile | |
| 900 | | | | | 905 | | | | | 910 | | | | | | |
| AAC | TTC | CAG | ACG | CCA | GGT | ATG | CTC | AGC | CAC | CCG | CCC | ATT | CCC | ATC | ACA | 3619 |
| Asn | Phe | Gln | Thr | Pro | Gly | Met | Leu | Ser | His | Pro | Pro | Ile | Pro | Ile | Thr | |
| 915 | | | | | 920 | | | | | 925 | | | | | | |
| GAC | ATG | GCT | GAA | CAC | ATG | GAG | AGA | CTC | AAA | GCC | AAC | GAC | AGC | CTC | AAG | 3667 |
| Asp | Met | Ala | Glu | His | Met | Glu | Arg | Leu | Lys | Ala | Asn | Asp | Ser | Leu | Lys | |
| 930 | | | | | 935 | | | | | 940 | | | | | 945 | |
| CTC | TCC | CAG | GAG | TAT | GAG | TCC | ATC | GAC | CCT | GGC | CAG | CAG | TTC | ACT | TGG | 3715 |
| Leu | Ser | Gln | Glu | Tyr | Glu | Ser | Ile | Asp | Pro | Gly | Gln | Gln | Phe | Thr | Trp | |
| | | | | 950 | | | | | 955 | | | | | 960 | | |
| GAA | CAT | TCG | AAC | CTG | GAG | GCC | AAC | AAG | CCA | AAG | AAC | CGA | TAC | GCC | AAT | 3763 |
| Glu | His | Ser | Asn | Leu | Glu | Ala | Asn | Lys | Pro | Lys | Asn | Arg | Tyr | Ala | Asn | |
| | | | 965 | | | | 970 | | | | | 975 | | | | |
| GTC | ATC | GCC | TAT | GAC | CAT | TCA | CGA | GTC | ATC | CTG | CAG | CCT | TTA | GAA | GGC | 3811 |
| Val | Ile | Ala | Tyr | Asp | His | Ser | Arg | Val | Ile | Leu | Gln | Pro | Leu | Glu | Gly | |
| | | 980 | | | | 985 | | | | 990 | | | | | | |
| ATC | ATG | GGT | AGT | GAT | TAC | ATC | AAT | GCC | AAC | TAT | GTG | GAC | GGC | TAT | CGG | 3859 |
| Ile | Met | Gly | Ser | Asp | Tyr | Ile | Asn | Ala | Asn | Tyr | Val | Asp | Gly | Tyr | Arg | |
| | 995 | | | | | 1000 | | | | | 1005 | | | | | |
| CGG | CAG | AAC | GCA | TAC | ATC | GCC | ACG | CAG | GGG | CCC | CTC | CCT | GAA | ACC | TTT | 3907 |
| Arg | Gln | Asn | Ala | Tyr | Ile | Ala | Thr | Gln | Gly | Pro | Leu | Pro | Glu | Thr | Phe | |
| 1010 | | | | | 1015 | | | | | 1020 | | | | | 1025 | |
| GGG | GAC | TTC | TGG | CGG | ATG | GTG | TGG | GAG | CAG | CGG | TCA | GCC | ACT | GTG | GTC | 3955 |
| Gly | Asp | Phe | Trp | Arg | Met | Val | Trp | Glu | Gln | Arg | Ser | Ala | Thr | Val | Val | |
| | | | | 1030 | | | | | 1035 | | | | | 1040 | | |
| ATG | ATG | ACA | CGG | CTG | GAG | GAG | AAA | TCA | CGG | GTC | AAA | TGT | GAC | CAG | TAC | 4003 |
| Met | Met | Thr | Arg | Leu | Glu | Glu | Lys | Ser | Arg | Val | Lys | Cys | Asp | Gln | Tyr | |
| | | | 1045 | | | | | 1050 | | | | | 1055 | | | |
| TGG | CCT | AAC | CGA | GGC | ACC | GAG | ACA | TAC | GGC | TTC | ATC | CAG | GTC | ACC | CTA | 4051 |
| Trp | Pro | Asn | Arg | Gly | Thr | Glu | Thr | Tyr | Gly | Phe | Ile | Gln | Val | Thr | Leu | |
| | | | 1060 | | | | 1065 | | | | | 1070 | | | | |
| CTA | GAT | ACT | ATG | GAG | CTG | GCC | ACC | TTC | TGT | GTC | AGG | ACC | TTT | TCT | CTA | 4099 |
| Leu | Asp | Thr | Met | Glu | Leu | Ala | Thr | Phe | Cys | Val | Arg | Thr | Phe | Ser | Leu | |
| | 1075 | | | | | 1080 | | | | | 1085 | | | | | |
| CAC | AAG | AAT | GGC | TCT | AGT | GAG | AAG | CGT | GAG | GTA | CGA | CAT | TTT | CAG | TTC | 4147 |
| His | Lys | Asn | Gly | Ser | Ser | Glu | Lys | Arg | Glu | Val | Arg | His | Phe | Gln | Phe | |
| 1090 | | | | | 1095 | | | | | 1100 | | | | | 1105 | |
| ACA | GCA | TGG | CCT | GAC | CAC | GGG | GTA | CCC | GAG | TAC | CCC | ACA | CCC | TTC | CTG | 4195 |
| Thr | Ala | Trp | Pro | Asp | His | Gly | Val | Pro | Glu | Tyr | Pro | Thr | Pro | Phe | Leu | |
| | | | | 1110 | | | | | 1115 | | | | | 1120 | | |
| GCG | TTT | CTG | CGC | AGA | GTC | AAG | ACC | TGC | AAC | CCG | CCT | GAC | GCT | GGC | CCA | 4243 |
| Ala | Phe | Leu | Arg | Arg | Val | Lys | Thr | Cys | Asn | Pro | Pro | Asp | Ala | Gly | Pro | |
| | | | | 1125 | | | | | 1130 | | | | | 1135 | | |
| GTT | GTG | GTC | CAC | TGC | AGC | GCG | GGT | GTG | GGG | CGT | ACT | GGC | TGC | TTC | ATT | 4291 |
| Val | Val | Val | His | Cys | Ser | Ala | Gly | Val | Gly | Arg | Thr | Gly | Cys | Phe | Ile | |
| | | | 1140 | | | | | 1145 | | | | | 1150 | | | |
| GTA | ATT | GAT | GCC | ATG | TTG | GAG | CGC | ATC | AGA | ACA | GAG | AAG | ACG | GTG | GAT | 4339 |
| Val | Ile | Asp | Ala | Met | Leu | Glu | Arg | Ile | Arg | Thr | Glu | Lys | Thr | Val | Asp | |
| | | | 1155 | | | | | 1160 | | | | | 1165 | | | |
| GTG | TAC | GGA | CAC | GTG | ACA | CTC | ATG | CGG | TCA | CAG | CGC | AAC | TAC | ATG | GTG | 4387 |
| Val | Tyr | Gly | His | Val | Thr | Leu | Met | Arg | Ser | Gln | Arg | Asn | Tyr | Met | Val | |
| 1170 | | | | | 1175 | | | | | 1180 | | | | | 1185 | |
| CAG | ACA | GAG | GAT | CAG | TAT | AGC | TTC | ATC | CAC | GAG | GCA | CTG | CTG | GAG | GCT | 4435 |
| Gln | Thr | Glu | Asp | Gln | Tyr | Ser | Phe | Ile | His | Glu | Ala | Leu | Leu | Glu | Ala | |
| | | | | 1190 | | | | | 1195 | | | | | 1200 | | |

| | | | | | | | | | | | | | | | | |
|---|---|---|---|---|---|---|---|---|---|---|---|---|---|---|---|---|
| GTG | GGC | TGT | GGC | AAT | ACC | GAG | GTC | CCC | GCG | CGC | AGC | CTC | TAC | ACC | TAT | 4483 |
| Val | Gly | Cys | Gly | Asn | Thr | Glu | Val | Pro | Ala | Arg | Ser | Leu | Tyr | Thr | Tyr | |
| | | | | 1205 | | | 1210 | | | | | 1215 | | | | |
| ATC | CAG | AAG | CTG | GCC | CAG | GTG | GAG | CCT | GGC | GAG | CAT | GTC | ACA | GGA | ATG | 4531 |
| Ile | Gln | Lys | Leu | Ala | Gln | Val | Glu | Pro | Gly | Glu | His | Val | Thr | Gly | Met | |
| | | | 1220 | | | | 1225 | | | | | 1230 | | | | |
| GAG | CTT | GAG | TTC | AAG | AGG | CTT | GCC | AGC | TCC | AAG | GCA | CAC | ACT | TCG | AGA | 4579 |
| Glu | Leu | Glu | Phe | Lys | Arg | Leu | Ala | Ser | Ser | Lys | Ala | His | Thr | Ser | Arg | |
| | | 1235 | | | | | 1240 | | | | | 1245 | | | | |
| TTC | ATC | ACT | GCC | AGC | CTG | CCT | TGC | AAC | AAG | TTT | AAG | AAC | CGC | CTG | GTG | 4627 |
| Phe | Ile | Thr | Ala | Ser | Leu | Pro | Cys | Asn | Lys | Phe | Lys | Asn | Arg | Leu | Val | |
| 1250 | | | | | 1255 | | | | | 1260 | | | | | 1265 | |
| AAC | ATC | CTG | CCG | TAC | GAG | AGC | TCG | CGT | GTC | TGC | CTG | CAG | CCC | ATT | CGT | 4675 |
| Asn | Ile | Leu | Pro | Tyr | Glu | Ser | Ser | Arg | Val | Cys | Leu | Gln | Pro | Ile | Arg | |
| | | | 1270 | | | | 1275 | | | | | 1280 | | | | |
| GGT | GTC | GAG | GGC | TCT | GAC | TAC | ATC | AAT | GCC | AGC | TTC | ATC | GAC | GGC | TAC | 4723 |
| Gly | Val | Glu | Gly | Ser | Asp | Tyr | Ile | Asn | Ala | Ser | Phe | Ile | Asp | Gly | Tyr | |
| | | | | 1285 | | | | 1290 | | | | | 1295 | | | |
| AGA | CAG | CAG | AAA | GCC | TAC | ATT | GCA | ACG | CAG | GGT | CCA | CTG | GCA | GAG | ACC | 4771 |
| Arg | Gln | Gln | Lys | Ala | Tyr | Ile | Ala | Thr | Gln | Gly | Pro | Leu | Ala | Glu | Thr | |
| | | 1300 | | | | | 1305 | | | | | 1310 | | | | |
| ACA | GAG | GAC | TTC | TGG | CGT | GCC | CTG | TGG | GAG | AAC | AAC | TCC | ACT | ATT | GTG | 4819 |
| Thr | Glu | Asp | Phe | Trp | Arg | Ala | Leu | Trp | Glu | Asn | Asn | Ser | Thr | Ile | Val | |
| | 1315 | | | | | 1320 | | | | | 1325 | | | | | |
| GTA | ATG | CTC | ACC | AAG | CTC | CGC | GAG | ATG | GGC | CGG | GAG | AAG | TGC | CAC | CAG | 4867 |
| Val | Met | Leu | Thr | Lys | Leu | Arg | Glu | Met | Gly | Arg | Glu | Lys | Cys | His | Gln | |
| 1330 | | | | | 1335 | | | | | 1340 | | | | | 1345 | |
| TAC | TGG | CCA | GCT | GAG | CGC | TCT | GCC | CGC | TAC | CAG | TAC | TTT | GTG | GTT | GAC | 4915 |
| Tyr | Trp | Pro | Ala | Glu | Arg | Ser | Ala | Arg | Tyr | Gln | Tyr | Phe | Val | Val | Asp | |
| | | | | 1350 | | | | 1355 | | | | | 1360 | | | |
| CCG | ATG | GCA | GAG | TAT | AAC | ATG | CCA | CAG | TAC | ATT | CTG | CGT | GAG | TTT | AAG | 4963 |
| Pro | Met | Ala | Glu | Tyr | Asn | Met | Pro | Gln | Tyr | Ile | Leu | Arg | Glu | Phe | Lys | |
| | | | 1365 | | | | | 1370 | | | | | 1375 | | | |
| GTC | ACA | GAT | GCC | CGG | GAT | GGC | CAG | TCC | CGG | ACC | GTC | CGA | CAG | TTC | CAG | 5011 |
| Val | Thr | Asp | Ala | Arg | Asp | Gly | Gln | Ser | Arg | Thr | Val | Arg | Gln | Phe | Gln | |
| | | | 1380 | | | | 1385 | | | | | 1390 | | | | |
| TTC | ACG | GAC | TGG | CCA | GAG | CAG | GGT | GCA | CCC | AAG | TCA | GGG | GAA | GGC | TTC | 5059 |
| Phe | Thr | Asp | Trp | Pro | Glu | Gln | Gly | Ala | Pro | Lys | Ser | Gly | Glu | Gly | Phe | |
| | 1395 | | | | | 1400 | | | | | 1405 | | | | | |
| ATT | GAC | TTC | ATC | GGC | CAA | GTG | CAT | AAG | ACC | AAG | GAG | CAG | TTT | GGC | CAG | 5107 |
| Ile | Asp | Phe | Ile | Gly | Gln | Val | His | Lys | Thr | Lys | Glu | Gln | Phe | Gly | Gln | |
| 1410 | | | | | 1415 | | | | | 1420 | | | | | 1425 | |
| GAT | GGC | CCC | ATC | TCG | GTG | CAC | TGT | AGT | GCT | GGA | GTG | GGC | AGG | ACC | GGA | 5155 |
| Asp | Gly | Pro | Ile | Ser | Val | His | Cys | Ser | Ala | Gly | Val | Gly | Arg | Thr | Gly | |
| | | | | 1430 | | | | 1435 | | | | | 1440 | | | |
| GTA | TTC | ATC | ACT | CTG | AGC | ATC | GTG | CTG | GAG | CGA | ATG | CGC | TAC | GAG | GGG | 5203 |
| Val | Phe | Ile | Thr | Leu | Ser | Ile | Val | Leu | Glu | Arg | Met | Arg | Tyr | Glu | Gly | |
| | | | 1445 | | | | | 1450 | | | | | 1455 | | | |
| GTG | GTG | GAC | ATT | TTC | CAG | ACA | GTG | AAG | GTG | CTT | CGG | ACC | CAG | CGG | CCT | 5251 |
| Val | Val | Asp | Ile | Phe | Gln | Thr | Val | Lys | Val | Leu | Arg | Thr | Gln | Arg | Pro | |
| | | | 1460 | | | | 1465 | | | | | 1470 | | | | |
| GCC | ATG | GTG | CAG | ACA | GAG | GAT | GAG | TAC | CAG | TTC | TGC | TTC | CAG | GCG | GCG | 5299 |
| Ala | Met | Val | Gln | Thr | Glu | Asp | Glu | Tyr | Gln | Phe | Cys | Phe | Gln | Ala | Ala | |
| | | 1475 | | | | | 1480 | | | | | 1485 | | | | |
| TTG | GAA | TAC | CTG | GGC | AGC | TTT | GAT | CAT | TAT | GCA | ACA | TAAGCCATGG | | | | 5345 |
| Leu | Glu | Tyr | Leu | Gly | Ser | Phe | Asp | His | Tyr | Ala | Thr | | | | | |
| 1490 | | | | | 1495 | | | | | 1500 | | | | | | |
| GCCCCGCCCA | ACACCTCGAC | CCAGCTCCAA | GTGCCCTGAA | TGTGAGCCCA | GCCCTCGGTG | | | | | | | | | | | 5405 |
| CTGGGTGGGA | GGCGGCCCAG | GGAGGAAACC | TCCTCTCCCT | GGAGACAGGC | ACTGCCTTCG | | | | | | | | | | | 5465 |

```
GAAGGGCACA  TTCCTCATTC  CCTCCTGACT  CCAAAACGAG  GTTCCAGGGT  GGGGGGTAGG      5525

GTGGAGAGTA  GAGGAGGCAC  TGCTCCCCAT  AGCTGGGGTC  ACAAGGGACA  GAACTCTGCT      5585

CCCACACTTC  CCTGCCTGCC  TGTCAGCAAC  ATTCTTTTTT  TCCATTTTTT  TAATAGTGTA      5645

TTTTTTTTCT  TCATCTTTCT  TTTTTTTTTT  TAAAAAAAAA  AAAAA                      5690
```

(2) INFORMATION FOR SEQ ID NO:3:

(i) SEQUENCE CHARACTERISTICS:
        (A) LENGTH: 1501 amino acids
        (B) TYPE: amino acid
        (D) TOPOLOGY: linear (ii) MOLECULE TYPE: protein (xi) SEQUENCE DESCRIPTION: SEQ ID NO:3:

```
Met  Ala  Pro  Thr  Trp  Arg  Pro  Ser  Val  Val  Ser  Val  Val  Gly  Pro  Val
 1                  5                   10                  15

Gly  Leu  Phe  Leu  Val  Leu  Leu  Ala  Arg  Gly  Cys  Leu  Ala  Glu  Pro
            20                  25                  30

Pro  Arg  Phe  Ile  Arg  Glu  Pro  Lys  Asp  Gln  Ile  Gly  Val  Ser  Gly  Gly
            35                  40                  45

Val  Ala  Ser  Phe  Val  Cys  Gln  Ala  Thr  Gly  Asp  Pro  Lys  Pro  Arg  Val
50                       55                  60

Thr  Trp  Asn  Lys  Lys  Gly  Lys  Lys  Val  Asn  Ser  Gln  Arg  Phe  Glu  Thr
65                       70                  75                       80

Ile  Asp  Phe  Asp  Glu  Ser  Ser  Gly  Ala  Val  Leu  Arg  Ile  Gln  Pro  Leu
                    85                  90                       95

Arg  Thr  Pro  Arg  Asp  Glu  Asn  Val  Tyr  Glu  Cys  Val  Ala  Gln  Asn  Ser
                    100                 105                      110

Val  Gly  Glu  Ile  Thr  Val  His  Ala  Lys  Leu  Thr  Val  Leu  Arg  Glu  Asp
            115                 120                      125

Gln  Leu  Pro  Pro  Gly  Phe  Pro  Asn  Ile  Asp  Met  Gly  Pro  Gln  Leu  Lys
            130                 135                      140

Val  Val  Glu  Arg  Thr  Arg  Thr  Ala  Thr  Met  Leu  Cys  Ala  Ala  Ser  Gly
145                      150                      155                      160

Asn  Pro  Asp  Pro  Glu  Ile  Thr  Trp  Phe  Lys  Asp  Phe  Leu  Pro  Val  Asp
                    165                 170                      175

Pro  Ser  Ala  Ser  Asn  Gly  Arg  Ile  Lys  Gln  Leu  Arg  Ser  Gly  Ala  Leu
            180                 185                      190

Gln  Ile  Glu  Ser  Ser  Glu  Glu  Thr  Asp  Gln  Gly  Lys  Tyr  Glu  Cys  Val
            195                 200                      205

Ala  Thr  Asn  Ser  Ala  Gly  Val  Arg  Tyr  Ser  Ser  Pro  Ala  Asn  Leu  Tyr
     210                 215                      220

Val  Arg  Val  Arg  Arg  Val  Ala  Pro  Arg  Phe  Ser  Ile  Leu  Pro  Met  Ser
225                      230                      235                      240

His  Glu  Ile  Met  Pro  Gly  Gly  Asn  Val  Asn  Ile  Thr  Cys  Val  Ala  Val
                    245                 250                      255

Gly  Ser  Pro  Met  Pro  Tyr  Val  Lys  Trp  Met  Gln  Gly  Ala  Glu  Asp  Leu
                    260                 265                      270

Thr  Pro  Glu  Asp  Asp  Met  Pro  Val  Gly  Arg  Asn  Val  Leu  Glu  Leu  Thr
            275                 280                      285

Asp  Val  Lys  Asp  Ser  Ala  Asn  Tyr  Thr  Cys  Val  Ala  Met  Ser  Ser  Leu
     290                 295                      300

Gly  Val  Ile  Glu  Ala  Val  Ala  Gln  Ile  Thr  Val  Lys  Ser  Leu  Pro  Lys
305                      310                      315                      320
```

```
Ala  Pro  Gly  Thr  Pro  Val  Val  Thr  Glu  Asn  Thr  Ala  Thr  Ser  Ile  Thr
               325                      330                      335

Val  Thr  Trp  Asp  Ser  Gly  Asn  Pro  Asp  Pro  Val  Ser  Tyr  Tyr  Val  Ile
               340                      345                      350

Glu  Tyr  Lys  Ser  Lys  Ser  Gln  Asp  Gly  Pro  Tyr  Gln  Ile  Lys  Glu  Asp
               355                      360                      365

Ile  Thr  Thr  Thr  Arg  Tyr  Ser  Ile  Gly  Gly  Leu  Ser  Pro  Asn  Ser  Glu
     370                      375                      380

Tyr  Glu  Ile  Trp  Val  Ser  Ala  Val  Asn  Ser  Ile  Gly  Gln  Gly  Pro  Pro
385                      390                      395                      400

Ser  Glu  Ser  Val  Val  Thr  Arg  Thr  Gly  Glu  Gln  Ala  Pro  Ala  Ser  Ala
               405                      410                      415

Pro  Arg  Asn  Val  Gln  Ala  Arg  Met  Leu  Ser  Ala  Thr  Thr  Met  Ile  Val
               420                      425                      430

Gln  Trp  Glu  Glu  Pro  Val  Glu  Pro  Asn  Gly  Leu  Ile  Arg  Gly  Tyr  Arg
               435                      440                      445

Val  Tyr  Tyr  Thr  Met  Glu  Pro  Glu  His  Pro  Val  Gly  Asn  Trp  Gln  Lys
          450                      455                      460

His  Asn  Val  Asp  Asp  Ser  Leu  Leu  Thr  Thr  Val  Gly  Ser  Leu  Leu  Glu
465                      470                      475                      480

Asp  Glu  Thr  Tyr  Thr  Val  Arg  Val  Leu  Ala  Phe  Thr  Ser  Val  Gly  Asp
                    485                      490                      495

Gly  Pro  Leu  Ser  Asp  Pro  Ile  Gln  Val  Lys  Thr  Gln  Gln  Gly  Val  Pro
               500                      505                      510

Gly  Gln  Pro  Met  Asn  Leu  Arg  Ala  Glu  Ala  Lys  Ser  Glu  Thr  Ser  Ile
               515                      520                      525

Gly  Leu  Ser  Trp  Ser  Ala  Pro  Arg  Gln  Glu  Ser  Val  Ile  Lys  Tyr  Glu
     530                      535                      540

Leu  Leu  Phe  Arg  Glu  Gly  Asp  Arg  Gly  Arg  Glu  Val  Gly  Arg  Thr  Phe
545                      550                      555                      560

Asp  Pro  Thr  Thr  Ala  Phe  Val  Val  Glu  Asp  Leu  Lys  Pro  Asn  Thr  Glu
                    565                      570                      575

Tyr  Ala  Phe  Arg  Leu  Ala  Ala  Arg  Ser  Pro  Gln  Gly  Leu  Gly  Ala  Phe
               580                      585                      590

Thr  Ala  Val  Val  Arg  Gln  Arg  Thr  Leu  Gln  Ala  Ile  Ser  Pro  Lys  Asn
          595                      600                      605

Phe  Lys  Val  Lys  Met  Ile  Met  Lys  Thr  Ser  Val  Leu  Leu  Ser  Trp  Glu
610                      615                      620

Phe  Pro  Asp  Asn  Tyr  Asn  Ser  Pro  Thr  Pro  Tyr  Lys  Ile  Gln  Tyr  Asn
625                      630                      635                      640

Gly  Leu  Thr  Leu  Asp  Val  Asp  Gly  Arg  Thr  Thr  Lys  Lys  Leu  Ile  Thr
               645                      650                      655

His  Leu  Lys  Pro  His  Thr  Phe  Tyr  Asn  Phe  Val  Leu  Thr  Asn  Arg  Gly
               660                      665                      670

Ser  Ser  Leu  Gly  Gly  Leu  Gln  Gln  Thr  Val  Thr  Ala  Arg  Thr  Ala  Phe
          675                      680                      685

Asn  Met  Leu  Ser  Gly  Lys  Pro  Ser  Val  Ala  Pro  Lys  Pro  Asp  Asn  Asp
     690                      695                      700

Gly  Ser  Ile  Val  Val  Tyr  Leu  Pro  Asp  Gly  Gln  Ser  Pro  Val  Thr  Val
705                      710                      715                      720

Gln  Asn  Tyr  Phe  Ile  Val  Met  Val  Pro  Leu  Arg  Lys  Ser  Arg  Gly  Gly
               725                      730                      735

Gln  Phe  Pro  Ile  Leu  Leu  Gly  Ser  Pro  Glu  Asp  Met  Asp  Leu  Glu  Glu
               740                      745                      750
```

```
Leu Ile Gln Asp Leu Ser Arg Leu Gln Arg Arg Ser Leu Arg His Ser
        755                 760                 765

Arg Gln Leu Glu Val Pro Arg Pro Tyr Ile Ala Ala Arg Phe Ser Ile
770                 775                 780

Leu Pro Ala Val Phe His Pro Gly Asn Gln Lys Gln Tyr Gly Gly Phe
785                 790                 795                 800

Asp Asn Arg Gly Leu Glu Pro Gly His Arg Tyr Val Leu Phe Val Leu
                805                 810                 815

Ala Val Leu Gln Lys Asn Glu Pro Thr Phe Ala Ala Ser Pro Phe Ser
            820                 825                 830

Asp Pro Phe Gln Leu Asp Asn Pro Asp Pro Gln Pro Ile Val Asp Gly
            835                 840                 845

Glu Glu Gly Leu Ile Trp Val Ile Gly Pro Val Leu Ala Val Val Phe
850                 855                 860

Ile Ile Cys Ile Val Ile Ala Ile Leu Leu Tyr Lys Asn Lys Pro Asp
865                 870                 875                 880

Ser Lys Arg Lys Asp Ser Glu Pro Arg Thr Lys Cys Leu Leu Asn Asn
                885                 890                 895

Ala Asp Leu Ala Pro His His Pro Lys Asp Pro Val Glu Met Arg Arg
                900                 905                 910

Ile Asn Phe Gln Thr Pro Gly Met Leu Ser His Pro Pro Ile Pro Ile
            915                 920                 925

Thr Asp Met Ala Glu His Met Glu Arg Leu Lys Ala Asn Asp Ser Leu
930                 935                 940

Lys Leu Ser Gln Glu Tyr Glu Ser Ile Asp Pro Gly Gln Gln Phe Thr
945                 950                 955                 960

Trp Glu His Ser Asn Leu Glu Ala Asn Lys Pro Lys Asn Arg Tyr Ala
                965                 970                 975

Asn Val Ile Ala Tyr Asp His Ser Arg Val Ile Leu Gln Pro Leu Glu
                980                 985                 990

Gly Ile Met Gly Ser Asp Tyr Ile Asn Ala Asn Tyr Val Asp Gly Tyr
        995                 1000                1005

Arg Arg Gln Asn Ala Tyr Ile Ala Thr Gln Gly Pro Leu Pro Glu Thr
        1010                1015                1020

Phe Gly Asp Phe Trp Arg Met Val Trp Glu Gln Arg Ser Ala Thr Val
1025                1030                1035                1040

Val Met Met Thr Arg Leu Glu Glu Lys Ser Arg Val Lys Cys Asp Gln
                1045                1050                1055

Tyr Trp Pro Asn Arg Gly Thr Glu Thr Tyr Gly Phe Ile Gln Val Thr
                1060                1065                1070

Leu Leu Asp Thr Met Glu Leu Ala Thr Phe Cys Val Arg Thr Phe Ser
        1075                1080                1085

Leu His Lys Asn Gly Ser Ser Glu Lys Arg Glu Val Arg His Phe Gln
        1090                1095                1100

Phe Thr Ala Trp Pro Asp His Gly Val Pro Glu Tyr Pro Thr Pro Phe
1105                1110                1115                1120

Leu Ala Phe Leu Arg Arg Val Lys Thr Cys Asn Pro Pro Asp Ala Gly
                1125                1130                1135

Pro Val Val Val His Cys Ser Ala Gly Val Gly Arg Thr Gly Cys Phe
                1140                1145                1150

Ile Val Ile Asp Ala Met Leu Glu Arg Ile Arg Thr Glu Lys Thr Val
        1155                1160                1165

Asp Val Tyr Gly His Val Thr Leu Met Arg Ser Gln Arg Asn Tyr Met
```

|   | 1170 |   |   |   | 1175 |   |   |   | 1180 |   |   |   |   |   |
|---|---|---|---|---|---|---|---|---|---|---|---|---|---|---|

Val Gln Thr Glu Asp Gln Tyr Ser Phe Ile His Glu Ala Leu Leu Glu
1185     1190     1195     1200

Ala Val Gly Cys Gly Asn Thr Glu Val Pro Ala Arg Ser Leu Tyr Thr
    1205     1210     1215

Tyr Ile Gln Lys Leu Ala Gln Val Glu Pro Gly Glu His Val Thr Gly
    1220     1225     1230

Met Glu Leu Glu Phe Lys Arg Leu Ala Ser Ser Lys Ala His Thr Ser
    1235     1240     1245

Arg Phe Ile Thr Ala Ser Leu Pro Cys Asn Lys Phe Lys Asn Arg Leu
    1250     1255     1260

Val Asn Ile Leu Pro Tyr Glu Ser Ser Arg Val Cys Leu Gln Pro Ile
1265     1270     1275     1280

Arg Gly Val Glu Gly Ser Asp Tyr Ile Asn Ala Ser Phe Ile Asp Gly
    1285     1290     1295

Tyr Arg Gln Gln Lys Ala Tyr Ile Ala Thr Gln Gly Pro Leu Ala Glu
    1300     1305     1310

Thr Thr Glu Asp Phe Trp Arg Ala Leu Trp Glu Asn Asn Ser Thr Ile
    1315     1320     1325

Val Val Met Leu Thr Lys Leu Arg Glu Met Gly Arg Glu Lys Cys His
1330     1335     1340

Gln Tyr Trp Pro Ala Glu Arg Ser Ala Arg Tyr Gln Tyr Phe Val Val
1345     1350     1355     1360

Asp Pro Met Ala Glu Tyr Asn Met Pro Gln Tyr Ile Leu Arg Glu Phe
    1365     1370     1375

Lys Val Thr Asp Ala Arg Asp Gly Gln Ser Arg Thr Val Arg Gln Phe
    1380     1385     1390

Gln Phe Thr Asp Trp Pro Glu Gln Gly Ala Pro Lys Ser Gly Glu Gly
    1395     1400     1405

Phe Ile Asp Phe Ile Gly Gln Val His Lys Thr Lys Glu Gln Phe Gly
    1410     1415     1420

Gln Asp Gly Pro Ile Ser Val His Cys Ser Ala Gly Val Gly Arg Thr
1425     1430     1435     1440

Gly Val Phe Ile Thr Leu Ser Ile Val Leu Glu Arg Met Arg Tyr Glu
    1445     1450     1455

Gly Val Val Asp Ile Phe Gln Thr Val Lys Val Leu Arg Thr Gln Arg
    1460     1465     1470

Pro Ala Met Val Gln Thr Glu Asp Glu Tyr Gln Phe Cys Phe Gln Ala
    1475     1480     1485

Ala Leu Glu Tyr Leu Gly Ser Phe Asp His Tyr Ala Thr
    1490     1495     1500

( 2 ) INFORMATION FOR SEQ ID NO:4:

( i ) SEQUENCE CHARACTERISTICS:
  ( A ) LENGTH: 92 amino acids
  ( B ) TYPE: amino acid
  ( C ) STRANDEDNESS: unknown
  ( D ) TOPOLOGY: unknown ( i i ) MOLECULE TYPE: protein ( x i ) SEQUENCE DESCRIPTION: SEQ ID NO:4:

Pro Val Phe Val Lys Val Pro Glu Asp Gln Thr Gly Leu Ser Gly Gly
1     5     10     15

Val Ala Ser Phe Val Cys Gln Ala Thr Gly Glu Pro Lys Pro Arg Ile
    20     25     30

```
Thr  Trp  Met  Lys  Lys  Gly  Lys  Lys  Val  Ser  Ser  Gln  Arg  Phe  Glu  Val
          35                  40                      45

Ile  Glu  Phe  Asp  Asp  Gly  Ala  Gly  Ser  Val  Leu  Arg  Ile  Gln  Pro  Leu
     50                  55                      60

Arg  Val  Gln  Arg  Asp  Glu  Ala  Ile  Tyr  Glu  Cys  Thr  Ala  Thr  Asn  Ser
65                       70                  75                              80

Leu  Gly  Glu  Ile  Asn  Thr  Ser  Ala  Lys  Leu  Ser  Val
                85                       90
```

( 2 ) INFORMATION FOR SEQ ID NO:5:

( i ) SEQUENCE CHARACTERISTICS:
        ( A ) LENGTH: 93 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:5:

```
Leu  Gln  Val  Asp  Ile  Val  Pro  Ser  Gln  Gly  Glu  Ile  Ser  Val  Gly  Glu
1                   5                       10                      15

Ser  Lys  Phe  Phe  Leu  Cys  Gln  Val  Ala  Gly  Asp  Ala  Lys  Asp  Lys  Asp
               20                  25                      30

Ile  Ser  Trp  Phe  Ser  Pro  Asn  Gly  Glu  Lys  Leu  Ser  Pro  Asn  Gln  Gln
          35                       40                      45

Arg  Ile  Ser  Val  Val  Trp  Asn  Asp  Asp  Ser  Ser  Thr  Leu  Thr  Ile
     50                       55                      60

Tyr  Asn  Ala  Asn  Ile  Asp  Asp  Ala  Gly  Ile  Tyr  Lys  Cys  Val  Val  Thr
65                       70                  75                              80

Ala  Glu  Asp  Gly  Thr  Gln  Ser  Glu  Ala  Thr  Val  Asn  Val
                85                       90
```

( 2 ) INFORMATION FOR SEQ ID NO:6:

( i ) SEQUENCE CHARACTERISTICS:
        ( A ) LENGTH: 92 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:6:

```
Lys  Pro  Pro  Ile  Asp  Leu  Val  Val  Thr  Glu  Thr  Thr  Ala  Thr  Ser  Val
1                   5                       10                      15

Thr  Leu  Thr  Trp  Asp  Ser  Gly  Asn  Thr  Glu  Pro  Val  Ser  Phe  Tyr  Gly
               20                  25                      30

Ile  Gln  Tyr  Arg  Ala  Ala  Gly  Thr  Asp  Gly  Pro  Phe  Gln  Glu  Val  Asp
          35                       40                      45

Gly  Val  Ala  Ser  Thr  Arg  Tyr  Ser  Ile  Gly  Gly  Leu  Ser  Pro  Phe  Ser
     50                       55                      60

Glu  Tyr  Ala  Phe  Arg  Val  Leu  Ala  Val  Asn  Ser  Ile  Gly  Arg  Gly  Pro
65                       70                  75                              80

Pro  Ser  Glu  Ala  Val  Arg  Ala  Arg  Thr  Gly  Glu  Gln
                85                       90
```

( 2 ) INFORMATION FOR SEQ ID NO:7:

( i ) SEQUENCE CHARACTERISTICS:
        ( A ) LENGTH: 91 amino acids ( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:7:

| Ser | Pro | Pro | Thr | Asn | Leu | His | Leu | Glu | Ala | Asn | Pro | Asp | Thr | Gly | Val |
|---|---|---|---|---|---|---|---|---|---|---|---|---|---|---|---|
| 1 | | | | 5 | | | | | 10 | | | | | 15 | |

| Leu | Thr | Val | Ser | Trp | Glu | Arg | Ser | Thr | Thr | Pro | Asp | Ile | Thr | Gly | Tyr |
|---|---|---|---|---|---|---|---|---|---|---|---|---|---|---|---|
| | | | 20 | | | | 25 | | | | | 30 | | | |

| Arg | Ile | Thr | Thr | Thr | Pro | Thr | Asn | Gly | Gln | Gln | Gly | Asn | Ser | Leu | Glu |
|---|---|---|---|---|---|---|---|---|---|---|---|---|---|---|---|
| | | 35 | | | | | 40 | | | | | 45 | | | |

| Glu | Val | Val | His | Ala | Asp | Gln | Ser | Ser | Cys | Thr | Phe | Asp | Asn | Leu | Ser |
|---|---|---|---|---|---|---|---|---|---|---|---|---|---|---|---|
| | 50 | | | | | 55 | | | | | 60 | | | | |

| Pro | Gly | Leu | Glu | Tyr | Asn | Val | Ser | Val | Tyr | Thr | Val | Lys | Asp | Asp | Lys |
|---|---|---|---|---|---|---|---|---|---|---|---|---|---|---|---|
| 65 | | | | | 70 | | | | | 75 | | | | | 80 |

| Glu | Ser | Val | Pro | Ile | Ser | Asp | Thr | Ile | Ile | Pro |
|---|---|---|---|---|---|---|---|---|---|---|
| | | | | 85 | | | | | 90 | |

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: modified_base
        ( B ) LOCATION: 15
        ( D ) OTHER INFORMATION: /mod_base=i
            / label= N ( x i ) SEQUENCE DESCRIPTION: SEQ ID NO:8:

GAYTAYATYA AYGCNAGYTT                                                     20

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:9:

| Asp | Tyr | Ile | Asn | Ala | Ser |
|---|---|---|---|---|---|
| 1 | | | | 5 | |

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: modified_base
        ( B ) LOCATION: 3
        ( D ) OTHER INFORMATION: /mod_base=i
            / label= N -continued ( i x ) FEATURE:
    ( A ) NAME/KEY: modified_base
    ( B ) LOCATION: 6
    ( D ) OTHER INFORMATION: /mod_base=i
        / label= N ( i x ) FEATURE:
    ( A ) NAME/KEY: modified_base
    ( B ) LOCATION: 18
    ( D ) OTHER INFORMATION: /mod_base=i
        / label= N ( x i ) SEQUENCE DESCRIPTION: SEQ ID NO:10:

AYNCCNGCRC TRCARTGNAC                                               20

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:11:

Val His Cys Ser Ala Gly
1               5

( 2 ) INFORMATION FOR SEQ ID NO:12:

( i ) SEQUENCE CHARACTERISTICS:
        ( A ) LENGTH: 50 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:12:

TAGACCACAA TGGAACCATC GTTGTCAGGC TTTGGGGCGA CACTAGGCTT                50